US012599421B2

(12) United States Patent
Alamin et al.

(10) Patent No.: US 12,599,421 B2
(45) Date of Patent: Apr. 14, 2026

(54) SACRAL TETHER ANCHOR AND METHODS OF USE

(71) Applicant: Empirical Spine, Inc., Morgan Hill, CA (US)

(72) Inventors: Todd Alamin, Woodside, CA (US); Louis Fielding, San Carlos, CA (US); Darin Gittings, Sunnyvale, CA (US); Hugues Malandain, Mountain View, CA (US); Anand Parikh, San Diego, CA (US); Eller Torres, Vista, CA (US); Ian Bennett, San Francisco, CA (US)

(73) Assignee: Empirical Spine, Inc., Morgan Hill, CA (US)

( * ) Notice: Subject to any disclaimer, the term of this patent is extended or adjusted under 35 U.S.C. 154(b) by 0 days.

(21) Appl. No.: 18/653,562

(22) Filed: May 2, 2024

(65) Prior Publication Data

US 2025/0107834 A1     Apr. 3, 2025

Related U.S. Application Data

(63) Continuation of application No. 17/941,008, filed on Sep. 8, 2022, now abandoned, which is a continuation
(Continued)

(51) Int. Cl.
*A61B 17/70* (2006.01)
*A61B 17/16* (2006.01)
(Continued)

(52) U.S. Cl.
CPC .......... *A61B 17/88* (2013.01); *A61B 17/1606* (2013.01); *A61B 17/7053* (2013.01);
(Continued)

(58) Field of Classification Search
CPC .. A61B 17/7055; A61B 7/7067; A61B 7/7058
(Continued)

(56) References Cited

U.S. PATENT DOCUMENTS

| | | | |
|---|---|---|---|
| 3,648,691 | A | 3/1972 | Lumb et al. |
| 4,643,178 | A | 2/1987 | Nastari et al. |
| | | (Continued) | |

FOREIGN PATENT DOCUMENTS

| | | |
|---|---|---|
| EP | 0322334 A1 | 6/1989 |
| FR | 2681525 A1 | 3/1993 |
| | (Continued) | |

OTHER PUBLICATIONS

Al Baz et al.: Modified Technique of Tension Band Wiring in Flexion Injuries of the Middle and Lower Cervical Spine. Spine 20(11):1241-1244 (1995).
(Continued)

*Primary Examiner* — Jan Christopher L Merene
(74) *Attorney, Agent, or Firm* — Wilson Sonsini Goodrich & Rosati

(57) ABSTRACT

A system for restricting flexion of a spinal segment in a patient comprises a constraint device having a tether structure and a compliance member coupled with the tether structure. The tether structure is adapted to be coupled with a superior spinous process and a sacrum. The system also includes an anchor member that is anchored to the sacrum. The anchor member has an attachment feature that is adapted to couple with the constraint device.

1 Claim, 32 Drawing Sheets

Related U.S. Application Data of application No. 17/020,463, filed on Sep. 14, 2020, now abandoned, which is a continuation of application No. 15/863,716, filed on Jan. 5, 2018, now abandoned, which is a continuation of application No. 15/279,046, filed on Sep. 28, 2016, now abandoned, which is a continuation of application No. 14/598,932, filed on Jan. 16, 2015, now abandoned, which is a continuation of application No. 13/963,786, filed on Aug. 9, 2013, now abandoned, which is a continuation of application No. 13/193,441, filed on Jul. 28, 2011, now Pat. No. 8,529,607, which is a continuation of application No. PCT/US2010/022767, filed on Feb. 1, 2010.

(60) Provisional application No. 61/149,224, filed on Feb. 2, 2009.

(51) Int. Cl.

| | |
|---|---|
| *A61B 17/84* | (2006.01) |
| *A61B 17/88* | (2006.01) |
| *A61B 17/86* | (2006.01) |

(52) U.S. Cl.

CPC ...... *A61B 17/7055* (2013.01); *A61B 17/7056* (2013.01); *A61B 17/7059* (2013.01); *A61B 17/7067* (2013.01); *A61B 17/846* (2013.01); *A61B 17/1604* (2013.01); *A61B 17/1671* (2013.01); *A61B 17/8605* (2013.01); *A61B 17/8863* (2013.01)

(58) Field of Classification Search

USPC ............. 606/248–250, 279, 280–299, 70–71

See application file for complete search history.

(56) References Cited

U.S. PATENT DOCUMENTS

| | | | |
|---|---|---|---|
| 4,743,260 A | | 5/1988 | Burton |
| 4,773,402 A | * | 9/1988 | Asher ................ A61B 17/7055 |
| | | | 606/250 |
| 4,966,600 A | | 10/1990 | Songer et al. |
| 5,011,494 A | | 4/1991 | Von et al. |
| 5,092,866 A | | 3/1992 | Breard et al. |
| 5,116,340 A | | 5/1992 | Songer et al. |
| 5,127,912 A | * | 7/1992 | Ray .................... A61B 17/7055 |
| | | | 606/250 |
| 5,180,393 A | | 1/1993 | Commarmond |
| 5,282,863 A | | 2/1994 | Burton |
| 5,395,374 A | | 3/1995 | Miller et al. |
| 5,415,658 A | | 5/1995 | Kilpela et al. |
| 5,415,661 A | | 5/1995 | Holmes |
| 5,449,361 A | | 9/1995 | Preissman |
| 5,456,722 A | | 10/1995 | Mcleod et al. |
| 5,462,542 A | | 10/1995 | Alesi, Jr. |
| 5,496,318 A | | 3/1996 | Howland et al. |
| 5,540,698 A | | 7/1996 | Preissman |
| 5,562,737 A | | 10/1996 | Graf |
| 5,609,634 A | | 3/1997 | Voydeville |
| 5,628,756 A | | 5/1997 | Barker, Jr. et al. |
| 5,645,599 A | | 7/1997 | Samani |
| 5,725,582 A | | 3/1998 | Bevan et al. |
| 5,902,305 A | | 5/1999 | Beger et al. |
| RE36,221 E | | 6/1999 | Breard et al. |
| 5,928,232 A | | 7/1999 | Howland et al. |
| 5,935,133 A | | 8/1999 | Wagner et al. |
| 5,964,769 A | | 10/1999 | Wagner et al. |
| 5,989,256 A | | 11/1999 | Kuslich et al. |
| 6,053,921 A | | 4/2000 | Wagner et al. |
| 6,197,028 B1 | * | 3/2001 | Ray .................... A61B 17/7041 |
| | | | 606/301 |
| 6,248,106 B1 | | 6/2001 | Ferree |
| 6,312,431 B1 | | 11/2001 | Asfora |

| | | | |
|---|---|---|---|
| 6,364,883 B1 | | 4/2002 | Santilli |
| 6,378,289 B1 | | 4/2002 | Trudeau et al. |
| 6,391,030 B1 | | 5/2002 | Wagner et al. |
| 6,436,099 B1 | | 8/2002 | Drewry et al. |
| 6,451,019 B1 | | 9/2002 | Zucherman et al. |
| 6,468,309 B1 | | 10/2002 | Lieberman |
| 6,582,433 B2 | | 6/2003 | Yun |
| 6,605,091 B1 | | 8/2003 | Iwanski |
| 6,626,944 B1 | | 9/2003 | Taylor |
| 6,629,975 B1 | | 10/2003 | Kilpela et al. |
| 6,652,527 B2 | | 11/2003 | Zucherman et al. |
| 6,652,585 B2 | | 11/2003 | Lange |
| 6,656,185 B2 | | 12/2003 | Gleason et al. |
| 6,669,729 B2 | | 12/2003 | Chin |
| 6,682,533 B1 | | 1/2004 | Dinsdale et al. |
| 6,689,140 B2 | | 2/2004 | Cohen |
| 6,689,168 B2 | | 2/2004 | Lieberman |
| 6,695,852 B2 | | 2/2004 | Gleason |
| 6,712,819 B2 | | 3/2004 | Zucherman et al. |
| 6,716,245 B2 | | 4/2004 | Pasquet et al. |
| 6,761,720 B1 | | 7/2004 | Senegas |
| 6,835,205 B2 | | 12/2004 | Atkinson et al. |
| 7,029,475 B2 | | 4/2006 | Panjabi |
| 7,163,558 B2 | | 1/2007 | Senegas et al. |
| 2002/0151978 A1 | | 10/2002 | Zacouto et al. |
| 2004/0024458 A1 | | 2/2004 | Senegas et al. |
| 2004/0106995 A1 | | 6/2004 | Le et al. |
| 2004/0116927 A1 | | 6/2004 | Graf |
| 2004/0117017 A1 | | 6/2004 | Pasquet et al. |
| 2004/0127989 A1 | | 7/2004 | Dooris et al. |
| 2004/0172132 A1 | | 9/2004 | Ginn |
| 2004/0243239 A1 | | 12/2004 | Taylor |
| 2005/0033435 A1 | | 2/2005 | Belliard et al. |
| 2005/0049708 A1 | | 3/2005 | Atkinson et al. |
| 2005/0192581 A1 | | 9/2005 | Molz et al. |
| 2005/0216017 A1 | | 9/2005 | Fielding et al. |
| 2006/0069447 A1 | | 3/2006 | Disilvestro et al. |
| 2006/0136060 A1 | | 6/2006 | Taylor |
| 2006/0240533 A1 | | 10/2006 | Sengupta et al. |
| 2007/0213829 A1 | | 9/2007 | Le et al. |
| 2007/0233096 A1 | | 10/2007 | Garcia-Bengochea |
| 2007/0299445 A1 | * | 12/2007 | Shadduck .......... A61B 17/7011 |
| | | | 606/100 |
| 2008/0009866 A1 | | 1/2008 | Alamin et al. |
| 2008/0108993 A1 | | 5/2008 | Bennett et al. |
| 2008/0177264 A1 | | 7/2008 | Alamin et al. |
| 2008/0262549 A1 | | 10/2008 | Bennett et al. |
| 2009/0076555 A1 | * | 3/2009 | Lowry ................. A61B 17/70 |
| | | | 606/280 |

FOREIGN PATENT DOCUMENTS

| | | |
|---|---|---|
| WO | WO-0128442 A1 | 4/2001 |
| WO | WO-0203882 A2 | 1/2002 |
| WO | WO-02051326 A1 | 7/2002 |
| WO | WO-02071960 A1 | 9/2002 |
| WO | WO-03045262 A2 | 6/2003 |
| WO | WO-2004052246 A1 | 6/2004 |
| WO | WO-2004073532 A1 | 9/2004 |
| WO | WO-2008051423 A1 | 5/2008 |
| WO | WO-2008051801 A2 | 5/2008 |
| WO | WO-2008051802 A2 | 5/2008 |
| WO | WO-2008051806 A2 | 5/2008 |

OTHER PUBLICATIONS

Dickman et al.: Comparative Mechanical Properties of Spinal Cable and Wire Fixation Systems1996 Scientific Program Committee. Spine 22:596-604 (1997).

Garner et al.: Development and preclinical testing of a new tension-band device for the spine: the Loop system. Eur. Spine J. S186-S191 (2002).

Heller et al.: Stability of different wiring techniques in segmental spinal instrumentation Arch. Orthopedic and Trauma Surgery 117(1-2):96-99 (1997).

(56)                References Cited

OTHER PUBLICATIONS

Leahy et al.: Mechanical testing of a flexible fixation device for the lumbar spine Proc. Inst. Mech. Eng. Part H: J. Eng. Med. 214(5):489-495 (2000).

Minns et al.: Preliminary design and experimental studies of a novel soft implant for correcting sagittal plane instability in the lumbar spine. Spine 22(16):1819-1825 (1997).

Miyasaka et al.: Radiographic analysis of lumbar motion in relation to lumbosacral stability: investigation of moderate and maximum motion. Spine 25(6):732-737 (2000).

Papp et al.: An In Vitro Study of the Biomechanical Effects of Flexible Stabilization on the Lumbar Spine. Spine 22(2):151-155 (1997).

Shepherd et al.: Slippage of a spinous process hook during flexion in a flexible fixation system for the lumbar spine. Medical Eng. Phys. 23(2):135-141 (2001).

Shepherd et al.: Spinous process strength. Spine 25(3):319-323 (2000).

Voydeville et al.: Ligamentoplastie intervertébrale avec cale souple dans les instabilités lombaires. Orthop Traumatol 2:259-264 (1992).

* cited by examiner

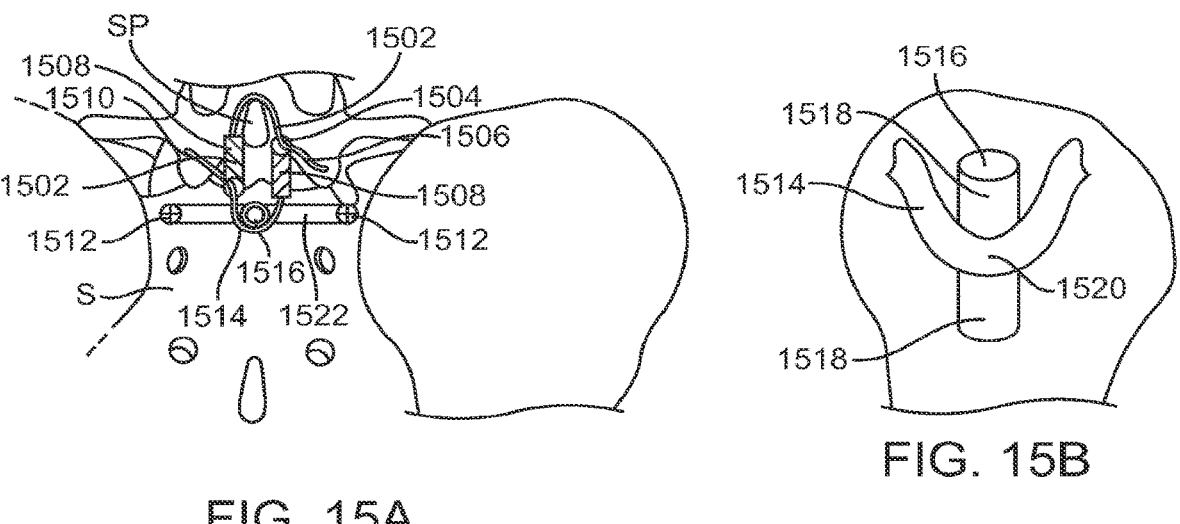
FIG. 15A
FIG. 15B
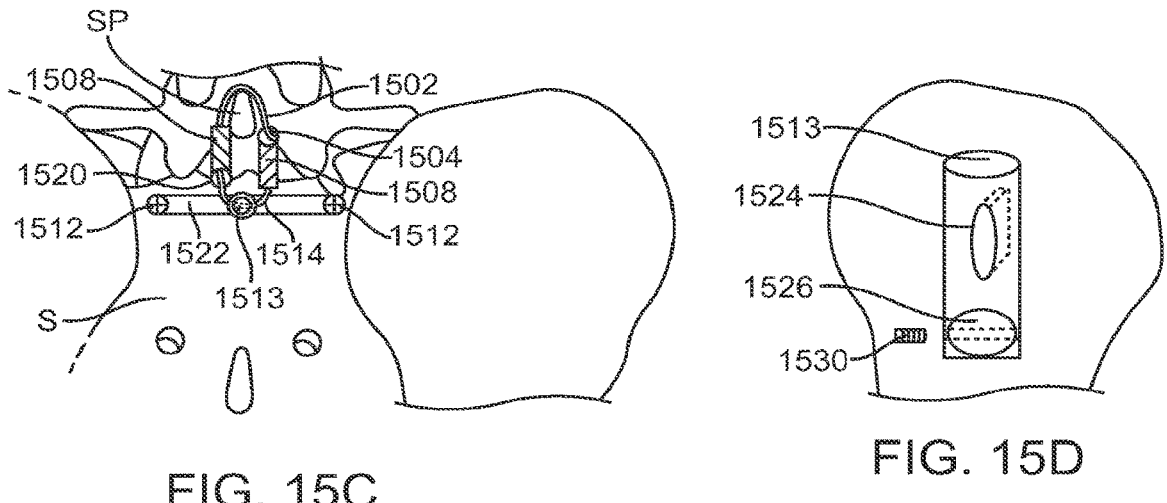
FIG. 15C
FIG. 15D 1708
1706
1710
1712
1702
1704

1708
1716
1718
1714
1720
1704

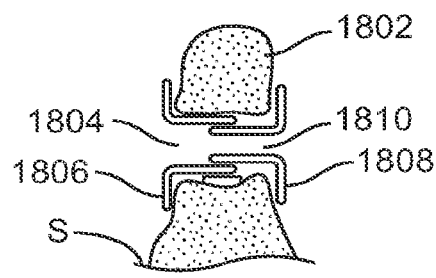
FIG. 18A
FIG. 18B
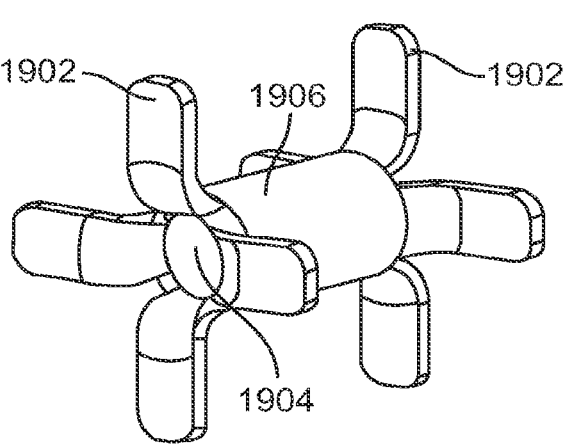
FIG. 19

SACRAL TETHER ANCHOR AND METHODS OF USE

CROSS-REFERENCES TO RELATED APPLICATIONS

The present application is a continuation of U.S. patent application Ser. No. 17/941,008, filed Sep. 8, 2022, which is a continuation of U.S. patent application Ser. No. 17/020, 463, filed Sep. 14, 2020, which is a continuation of U.S. patent application Ser. No. 15/863,716, filed Jan. 5, 2018, which is a continuation of U.S. patent application Ser. No. 15/279,046 filed Sep. 28, 2016 which is a continuation of U.S. patent application Ser. No. 14/598,932 filed Jan. 16, 2015, which is a continuation of U.S. patent application Ser. No. 13/963,786 filed Aug. 9, 2013, which is a continuation of U.S. patent application Ser. No. 13/193,441, filed Jul. 28, 2011, which is a continuation of PCT Application No. PCT/US2010/022767, filed Feb. 1, 2010, which claims the benefit of U.S. Provisional Patent Application No. 61/149, 224 filed Feb. 2, 2009; the entire contents of which are incorporated herein by reference.

BACKGROUND OF THE INVENTION

1. Field of the Invention

The present invention generally relates to medical methods and apparatus. More particularly, the present invention relates to methods and apparatus used to couple a prosthesis to a spinal segment. Often, a portion of the prosthesis may be coupled to the sacrum. The methods and apparatus disclosed herein may be used during orthopedic internal fixation procedures. This includes but is not limited to treatment of patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. Discogenic pain can be quite disabling, and for some patients, can dramatically affect their ability to work and otherwise enjoy their lives.

Pain experienced by patients with discogenic low back pain can be thought of as flexion instability, and is related to flexion instability manifested in other conditions. The most prevalent of these is spondylolisthesis, a spinal condition in which abnormal segmental translation is exacerbated by segmental flexion. The methods and devices described herein should as such also be useful for these other spinal disorders or treatments associated with segmental flexion, for which the prevention or control of spinal segmental flexion is desired. Another application for which the methods and devices described herein may be used is in conjunction with a spinal fusion, in order to restrict motion, promote healing, and relieve pain post-operatively. Alternatively, the methods and devices described should also be useful in conjunction with other treatments of the anterior column of the spine, including kyphoplasty, total disc replacement, nucleus augmentation and annular repair.

Patients with discogenic pain accommodate their syndrome by avoiding positions such as sitting, which cause their painful segment to go into flexion, preferring positions such as standing, which maintain their painful segment in extension. One approach to reducing discogenic pain involves the use of a lumbar support pillow often seen attached to office chairs. Biomechanically, the attempted effect of the ubiquitous lumbar support pillow is also to maintain the painful lumbar segment in the less painful extension position.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion may or may not also include instrumentation of the affected spinal segment including, for example, pedicle screws and stabilization rods. Fusion is not lightly recommended for discogenic pain because it is irreversible, costly, associated with high morbidity, and has questionable effectiveness. Despite its drawbacks, however, spinal fusion for discogenic pain remains common due to the lack of viable alternatives.

An alternative method, that is not commonly used in practice, but has been approved for use by the United States Food and Drug Administration (FDA), is the application of bone cerclage devices which can encircle the spinous processes or other vertebral elements and thereby create a restraint to motion. Physicians typically apply a tension or elongation to the devices so that they apply a constant and high force on the anatomy, thereby fixing the segment in one position and allowing effectively no motion. The lack of motion allowed after the application of such devices is thought useful to improve the likelihood of fusion performed concomitantly; if the fusion does not take, these devices will fail through breakage of the device or of the spinous process to which the device is attached. These devices are designed for static applications and are not designed to allow for dynamic elastic resistance to flexion across a range of motion. The purpose of bone cerclage devices and other techniques described above is to almost completely restrict measurable motion of the vertebral segment of interest. This loss of motion at a given segment gives rise to abnormal loading and motion at adjacent segments, which can lead eventually to adjacent segment morbidity.

An alternative solution that avoids some of the challenges associated with cerclage devices involves the use of an elastic structure, such as tether structures, coupled to the spinal segment. The elastic structure can relieve pain by increasing passive resistance to flexion while often allowing substantially unrestricted spinal extension. This mimics the mechanical effect of postural accommodations that patients already use to provide relief.

Spinal implants using tether structures are currently commercially available. One such implant couples adjacent vertebrae via their pedicles. This implant includes spacers, tethers and pedicle screws. To install the implant, muscles are retracted to a wide extent to expose the pedicles, and selected portions of the disc and vertebrae bone may be removed. Implants are then placed to couple two adjacent pedicles on each side of the spine. The pedicle screws secure the implants in place. The tether is clamped to the pedicle screws with set-screws, and limits the extension/flexion movements of the vertebrae of interest, as well as limiting other motions such as axial compression, later bending, and rotation. Because significant tissue is displaced and/or removed and because of screw placement into the pedicles, the implant and accompanying surgical methods are highly invasive and the implant is often irreversibly implanted. There is also an accompanying significant chance of nerve root damage. Additionally, the tip of the set-screw clamps the tethers, and this may result in abrasion of the tethers along with generation of particulate wear debris.

Other implants employing tether structures couple adjacent vertebrae via their processes instead. These implants include a tether and a spacer. To install the implant, the supraspinous ligament is temporarily lifted and displaced. The interspinous ligament between the two adjacent vertebrae of interest is then permanently removed and the spacer is inserted in the interspinous space. The tether is then wrapped around the processes of the two adjacent vertebrae, through adjacent interspinous ligaments, and then mechanically secured in place by the spacer or also by a separate component fastened to the spacer. The supraspinous ligament is then restored back to its original position. Such implants and accompanying surgical methods are not without disadvantages. These implants may subject the spinous processes to frequent, high loads during everyday activities, sometimes causing the spinous processes to break or erode. Furthermore, the spacer may put a patient into segmental kyphosis, potentially leading to long-term clinical problems associated with lack of sagittal balance. The process of securing the tethers is often a very complicated maneuver for a surgeon to perform, making the surgery much more invasive. And, as previously mentioned, the removal of the interspinous ligament is permanent. As such, the application of the device is not reversible.

More recently, less invasive spinal implants have been introduced. Like the aforementioned implant, these spinal implants are placed over one or more pairs of spinous processes and provide an elastic restraint to the spreading apart of the spinous processes occurring during flexion. However, extension-limiting spacers are not used and interspinous ligaments need not be permanently removed. As such, these implants are less invasive and may be reversibly implanted. The implants typically include a tether structure and a securing mechanism for the tether. The tether may be made from a flexible polymeric textile such as woven polyester (PET) or polyethylene (e.g. ultra high molecular weight polyethylene, UHMWPE); multi-strand cable, or other flexible structure. The tether is wrapped around the processes of adjacent vertebrae and then secured by the securing mechanism. Securing mechanisms are described in greater detail below.

While the constraint devices described above appear to be promising, in some situations, attachment of the device to a spinous process can be challenging. For example, if the constraint device is attached to a small spinous process that does not protrude enough or has geometry unsuitable to engage a tether, such as steeply sloping surfaces, the constraint device could migrate or disengage from the spinous process after implantation. Furthermore, it may be necessary to couple the constraint device with an upper spinous process disposed on a superior vertebra and an inferior spinous process, crest or tubercle disposed on the sacrum (e.g. for implantation at the L5-S1 level). Often, the spinous processes in these regions are small and do not protrude sufficiently to provide an adequate attachment point for the constraint device. In other cases where a spinous process of sufficient size is present, the surfaces may slope such that the constraint device would tend to migrate or slip off the process. Therefore, it would be desirable to provide apparatus and methods that facilitate attachment of the constraint device to a small or sloping spinous processes, sacral crest or tubercle, in particular one disposed on the sacrum or directly to the sacrum. Moreover, it would also be desirable if such devices and methods were easy to use and minimally invasive to the patient.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. 2002/0151978; 2004/0024458; 2004/0106995; 2004/0116927; 2004/0117017; 2004/0127989; 2004/0172132; 2004/0243239; 2005/0033435; 2005/0049708; 2005/0192581; 2005/0216017; 2006/0069447; 2006/0136060; 2006/0240533; 2007/0213829; 2007/0233096; 2008/0009866; 2008/0108993; 2008/0177264; 2008/0108993; 2008/0262549; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; WO2008/051806; WO2008/051423; WO2008/051801; WO2008/051802; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention relates to methods and apparatus used to couple a prosthesis to a spinal segment and adjust the prosthesis during orthopedic internal fixation procedures. This includes but is not limited to coupling a constraint device between a superior spinous process and the sacrum during treatment of patients having spinal pain, instability or other spinal conditions.

In a first aspect of the present invention, a system for restricting flexion of a spinal segment in a patient comprises a constraint device having a tether structure and a compliance member coupled with the tether structure. The tether structure comprises an upper portion adapted to be coupled with a superior spinous process and a lower portion adapted to be coupled with a sacrum. The constraint device provides a force resistant to flexion of the spinal segment. The system also has an anchor member comprising an attachment member and a coupling member. The attachment member is adapted to attach the anchor member to the sacrum, and the coupling member is adapted to couple the tether structure with the anchor member.

The system may further comprise a second compliance member coupled with the tether structure. The compliance members may be disposed substantially parallel to one another. They may be disposed on opposite sides of a midline of the spinal segment. The upper portion of the tether structure may comprise first and second free ends. Each of the free ends may be coupled with one of the compliance members. The lower portion of the tether structure may comprise a loop which may be coupled to the coupling member.

The anchor member may comprise an elongate bar, and the bar may be disposed across the midline of the spinal segment. The bar may comprise a through hole that is adapted to receive the attachment member, which attaches the bar to the sacrum. The bar may have an adjustable length. The anchor member may comprise a plate in engagement with the sacrum. The anchor may be disposed in a recessed region of the sacrum so that an outer surface of the anchor member is substantially flush with an outer surface of the sacrum. The anchor member may comprise a staple, or a cable.

The attachment member may comprise a screw threadably engaged with the sacrum. The screw may be axially threaded into engagement with a crest of the sacrum in a generally caudal direction. The attachment member may comprise a nail, a clip, or a hook that is adapted to couple with the sacrum.

The coupling member may comprise one of a hook, an eyelet, a slot, and a pin. The coupling member may comprise a channel disposed in a portion of the anchor member. The channel may be adapted to receive the tether structure therethrough. The system may further comprise a liner element disposed in the channel. The coupling member may comprise a protuberance adapted to engage the tether structure, or the coupling member may comprise a pin that is adapted to engage the tether structure. The coupling member may comprise a gate mechanism having an open position and a closed position. In the open position, the coupling member may receive the tether structure and in the closed position, the tether structure may be captured by the coupling member.

The system may further comprise a bone removal tool. The bone removal tool may be configured to remove bone from the sacrum thereby facilitating attachment of the anchor member thereto. The bone removal tool may comprise a rongeur tool, or a drill. The bone removal tool may comprise an elongate shaft, a handle coupled with the shaft, and a cutting element having a crescent shaped cross-section. The cutting element may extend laterally from the shaft, and it may be adapted to remove bone from the sacrum. The bone removal tool may comprise a knurled cutting surface adapted to remove bone from the sacrum.

The anchor member may comprise a surface that is adapted to promote osseointegration of the anchor with the sacrum. The surface may comprise hydroxyapatite or titanium.

In another aspect of the present invention, a system for restricting flexion of a spinal segment in a patient comprises a constraint device comprising a tether structure and a compliance member coupled with the tether structure. The tether structure comprises an upper portion and a lower portion. The upper portion is adapted to be coupled with a superior spinous process and the lower portion is adapted to be coupled with a coccyx. The constraint device provides a force resistant to flexion of the spinal segment. The lower portion may comprise a loop and the loop may be disposed around the coccyx. The lower portion may be longer than the upper portion.

In still another aspect of the present invention, a method for restricting flexion in a spinal segment comprises providing a constraint device having a tether structure, a compliance member coupled with the tether structure, and an anchor member. The tether structure comprises an upper portion and a lower portion. The upper portion of the tether structure is engaged with a superior spinous process, and the anchor member is attached to a sacrum. The lower portion of the tether structure is coupled with the anchor member.

The method may further comprise resisting flexion of the spinal segment. The step of engaging the upper portion of the tether structure may comprise disposing the upper portion of the tether structure over a superior surface of the spinous process.

The step of attaching the anchor member may comprise removing bone from the sacrum. Attaching the anchor member may comprise forming a recessed region in the sacrum. Attaching the anchor member may comprise creating a notched region or a channel in a crest of the sacrum. The attaching step may also comprise adjusting length of the anchor member. Attaching the anchor member may comprise threadably engaging a fastener with the sacrum. The fastener may be threadably engaged in a generally caudal direction so as to avoid penetration of the fastener into a spinal canal or into an anterior cortex of the sacrum. Attaching may comprise stapling or nailing the anchor member to the sacrum, or clipping a portion of the anchor member to a sacral crest or a spinous process of the sacrum. Attaching the anchor member may comprise hooking a portion of the anchor member with a neural foramen of the sacrum, or with a lateral edge of the sacrum.

The anchor member may comprise a through hole, and the step of coupling the lower portion of the tether structure comprises advancing the lower portion of the tether structure through the through hole. The anchor member may comprise an elongate channel, and the step of coupling the lower portion of the tether structure may comprise advancing the lower portion of the tether structure through the elongate channel. The step of coupling the lower portion of the tether structure may comprise at least partially encircling the lower portion of the tether structure around a portion of the anchor member or the coupling member. Coupling the lower portion of the tether structure may comprise opening a gate in the anchor member thereby permitting the anchor member to receive the tether structure. The gate may also be closed, thereby capturing the tether structure. The method may further comprise promoting osseointegration of the anchor member with the sacrum, or adjusting length or tension in the constraint device.

In another aspect of the present invention, a method for restricting flexion of a spinal segment in a patient comprises providing a constraint device having a tether structure that
has an upper portion and a lower portion. The upper portion
of the tether structure is engaged with a superior spinous
process, and bone is removed from the sacrum in order to
form an attachment region in the bone. The lower portion of
the tether structure is coupled with the attachment region.

The method may further comprise resisting flexion of the
spinal segment. The constraint device may further comprise
a compliance member coupled with the tether structure. The
step of engaging the upper portion of the tether structure
may comprise disposing the upper portion of the tether
structure over a superior surface of the spinous process.

The step of removing bone may comprise creating a
channel extending through a crest of the sacrum. The
channel may be lined with a liner element. Removing bone
may comprise notching the sacrum, or it may comprise one
of cutting, grinding, drilling, filing, rasping, sawing, and
abrading the sacrum. Removing bone may comprise remov-
ing the bone with one of a rongeur tool, a cutting tool, a file,
a rasp, a saw, and a drill.

The step of coupling the lower portion of the tether
structure may comprise advancing the lower portion through
a channel in the sacrum. The method may further comprise
preserving ligaments or other anatomical structures disposed
along a midline of the spinal segment.

In still another aspect of the present invention, a method
for restricting flexion of a spinal segment in a patient
comprises providing a constraint device having a tether
structure, and a compliance member coupled with the tether
structure. The tether structure comprises an upper portion
and a lower portion. The upper portion of the tether structure
is engaged with a superior spinous process, and the lower
portion of the tether structure is coupled with a coccyx.
Coupling the lower portion may comprise encircling at least
a portion of the coccyx with the lower portion of the tether
structure. The lower portion of the tether structure may
comprise a loop, and the step of coupling the lower portion
may comprise placing the loop around the coccyx.

These and other embodiments are described in further
detail in the following description related to the appended
drawing figures.

BRIEF DESCRIPTION OF THE DRAWINGS

FIGS. 15A-15D illustrate additional embodiments of a
screw or pin as the anchor.

FIGS. 18A-18B illustrate a liner.

FIG. 19 illustrates another embodiment of a liner.

DETAILED DESCRIPTION OF THE
INVENTION

Figure 1A:
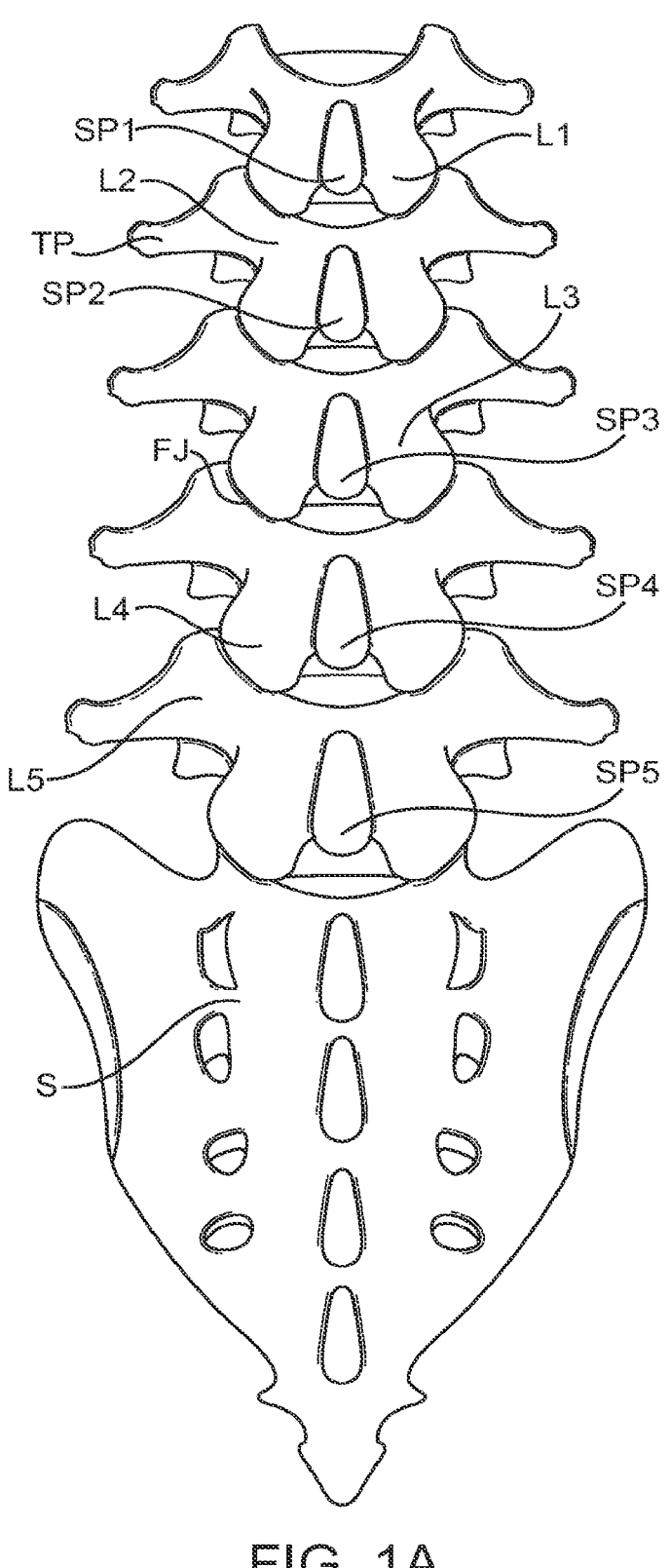
FIG. 1A is a schematic diagram illustrating the lumbar
and sacral regions of the spine.
Figure 1B:
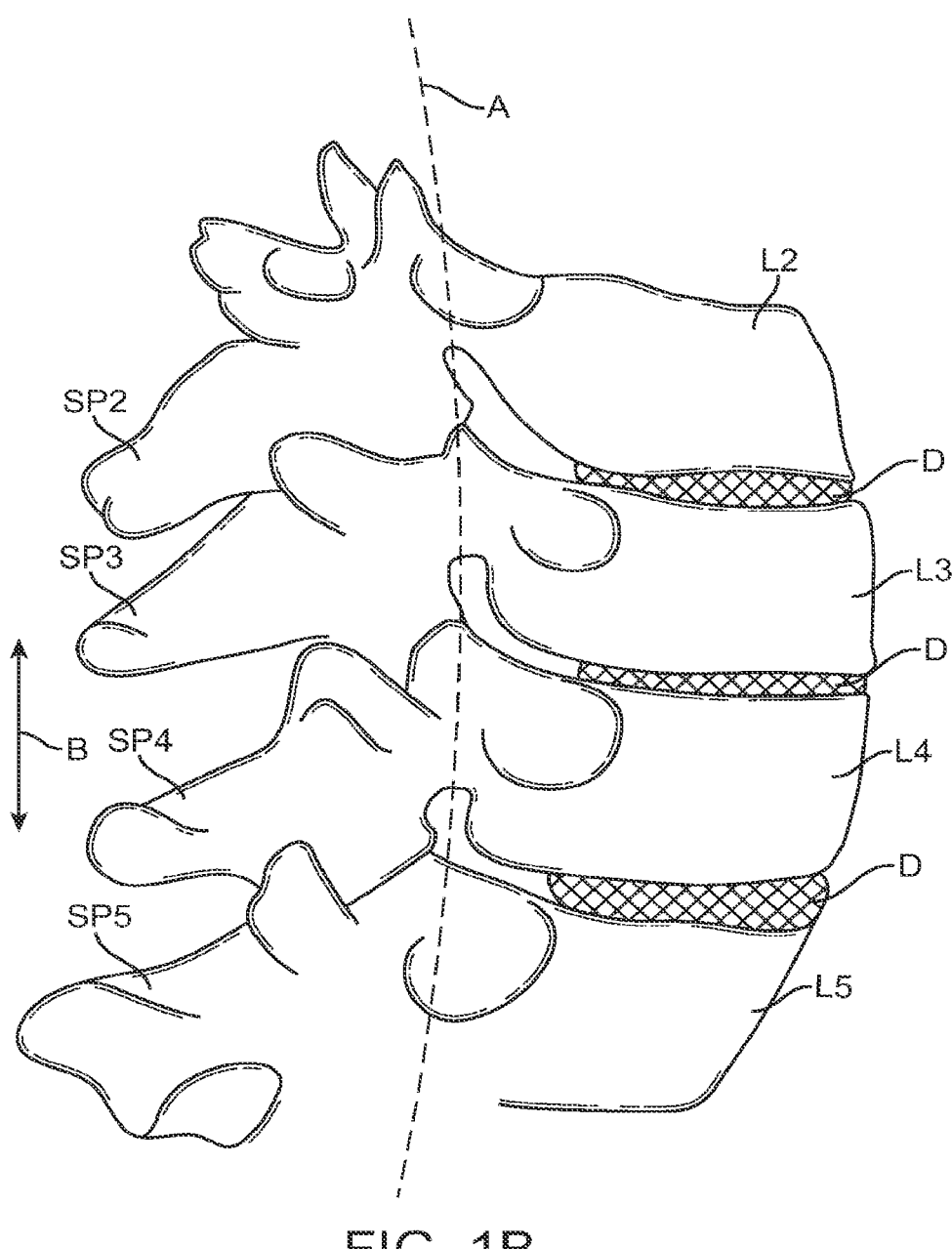
FIG. 1B a schematic illustration showing a portion of the
lumbar region of the spine taken along a sagittal plane.

FIG. 1A is a schematic diagram illustrating the lumbar
region of the spine including the spinous processes (SP),
facet joints (FJ), lamina (L), transverse processes (TP), and
sacrum(S). FIG. 1B is a schematic illustration showing a
portion of the lumbar region of the spine taken along a
sagittal plane and is useful for defining the terms "neutral
position," "flexion," and "extension" that are often used in
this disclosure.

As used herein, "neutral position" refers to the position in
which the patient's spine rests in a relaxed standing position.
The "neutral position" will vary from patient to patient.
Usually, such a neutral position will be characterized by a
slight curvature or lordosis of the lumbar spine where the
spine has a slight anterior convexity and slight posterior
concavity. In some cases, the presence of the constraint of
the present invention may modify the neutral position, e.g.
the device may apply an initial force which defines a "new"
neutral position having some extension of the untreated
spine. As such, the use of the term "neutral position" is to be
taken in context of the presence or absence of the device. As
used herein, "neutral position of the spinal segment" refers
to the position of a spinal segment when the spine is in the
neutral position.

Furthermore, as used herein, "flexion" refers to the
motion between adjacent vertebrae in a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Figure 2A:
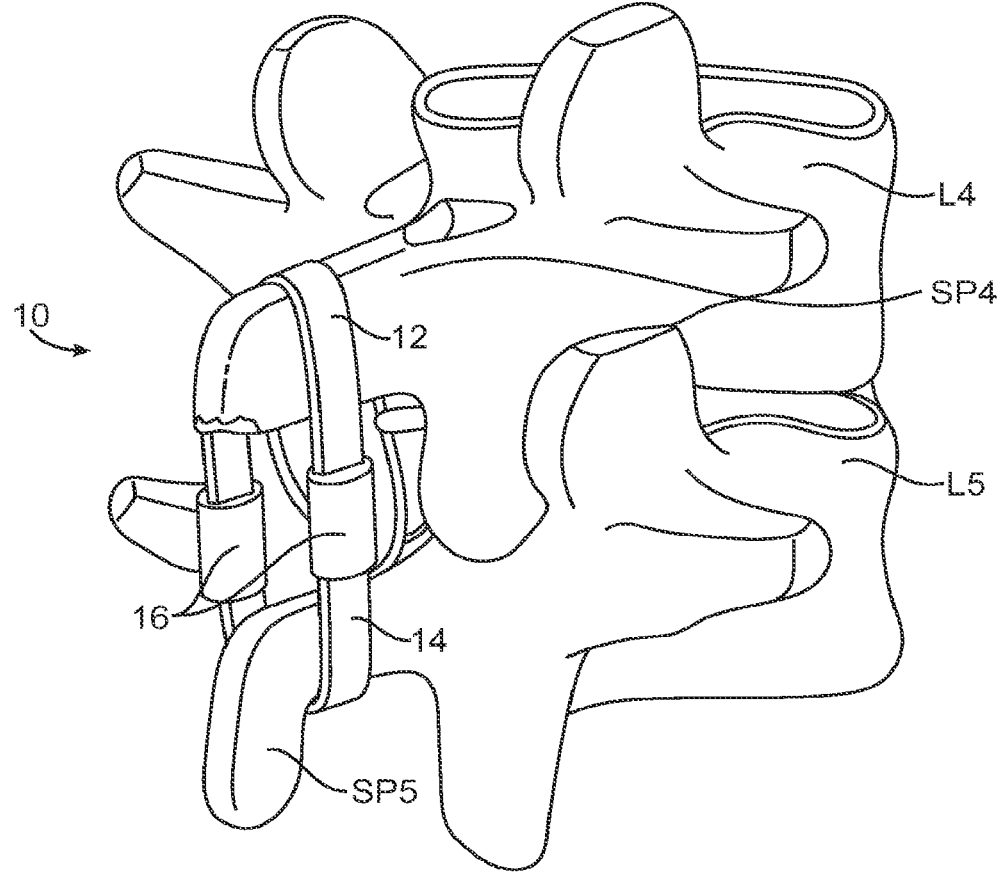
FIG. 2A illustrates a spinal implant of the type described
in U.S. Patent Publication No. 2005/0216017A1.

FIG. 2A shows a spinal implant of the type described in related U.S. Patent Publication No. 2005/0216017 A1 (now U.S. Pat. No. 7,458,981), the entire contents of which are incorporated herein by reference. As illustrated in FIG. 2A, an implant 10 typically comprises a tether structure having an upper strap component 12 and a lower strap component 14 joined by a pair of compliance elements 16. The upper strap 12 is shown disposed over the top of the spinous process SP4 of L4 while the lower strap 14 is shown extending over the bottom of the spinous process SP5 of L5. The compliance element 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance elements 16. Additional details on constraint devices is disclosed in U.S. patent application Ser. No. 12/106,103 which is incorporated herein by reference. Any of these constraint devices may be used with the anchoring methods and apparatus disclosed herein. In other embodiments, the constraint device may be a tether structure with or without a compliance member or element. The tether structure may be elastic.

Figure 2B:
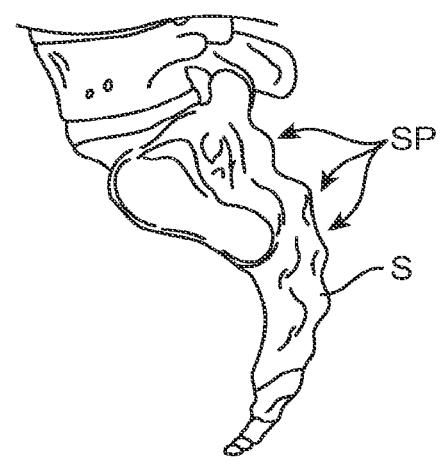
FIG. 2B illustrates the sacrum.

The flexion-limiting device may also be attached to an upper spinous process disposed on a vertebra and the sacrum in order to limit flexion between the sacrum and the upper vertebra. However, the sacrum often has spinous processes that are very short and rounded; these are also referred to as spinous tubercles. The sacrum may only have a low crest along the dorsal midline. These regions are often insufficient for a tether to loop around since the bone protruding from the sacrum may be too short and the oblique angle of the sacral surfaces around which the device would loop may permit the device to migrate dorsally, and potentially slide off. FIG. 2B illustrates the spinous processes SP on the sacrum.

Figure 3A:
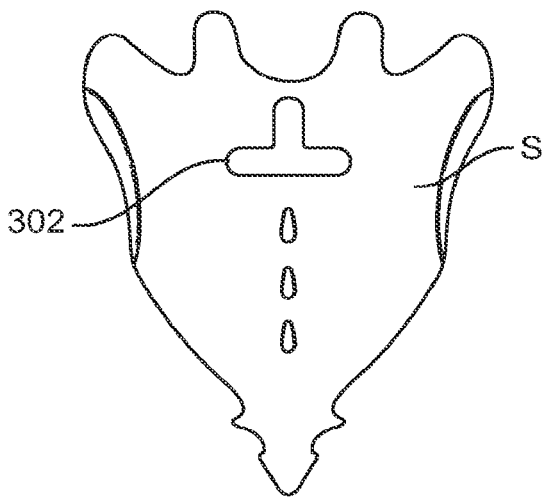
FIGS. 3A-3B illustrate the use of an undercut in the
sacrum for anchoring a constraint device.
Figure 3B:
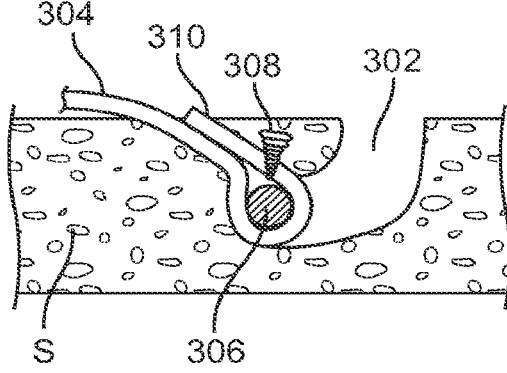

Referring now to FIG. 3A, a top view of the sacrum shows how an undercut 302 may be formed by carving, cutting, sawing, grinding or other suitable means, into the sacrum S. Undercut 302 in this exemplary embodiment is a T-shaped slot that is adapted to receive a pin or other anchor. FIG. 3B is a cross-sectional sideview of the sacrum and undercut 302. In FIG. 3B, a constraint device having a tether 304 is anchored to the sacrum S by engaging the tether 304 with the undercut 302. A free end 310 of tether 304 is wrapped around a pin 306 and the free end 310 is then fastened to the tether using methods well known in the art such as stitching, thermal welding, suturing, bonding, riveting, etc. Alternatively, the free end 310 may return to an attachment point on the constraint device. Tether 304 and pin 306 are then slidably received in the T-shaped slot 302, with the tether 304 exiting the central portion of slot 302. The tether 304 and pin 306 are advanced in the cranial direction until the pin 306 bottoms out in the slot thereby capturing the pin 306 and tether 304. An optional fastener 308, such as a screw or pin may be advanced through the sacrum and tether/pin in order to further secure the device into the slot 302. In this exemplary embodiment a T-shaped slot is used, however one will appreciate that other geometries may also be used. The remainder of the constraint device may be secured to a superior portion of the affected spinal segment such as a spinous process, pedicle, transverse process, etc. Tools which may be used to create the undercut are described below.

Figure 4A:
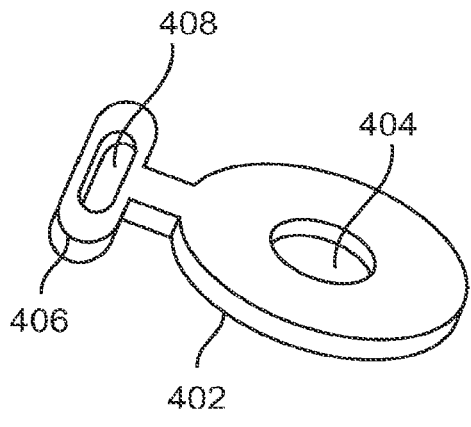
FIGS. 4A-4C illustrate the use of an anchor member for
securing a constraint device to the sacrum.
Figure 4B:
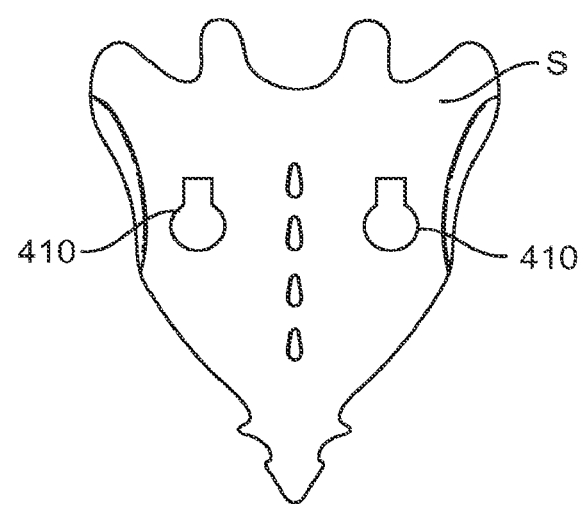
Figure 4C:
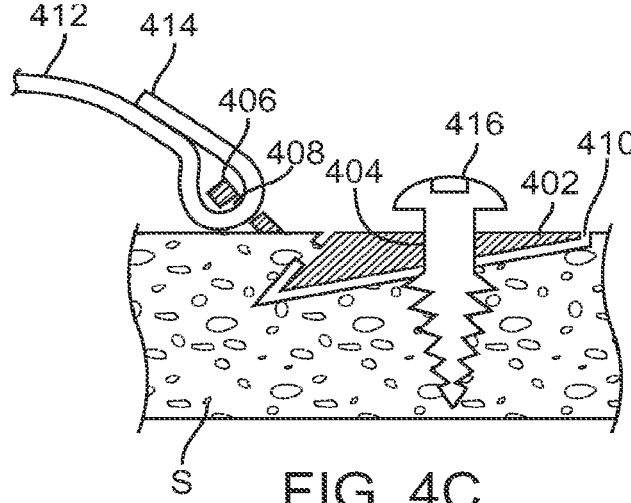

FIGS. 4A-4C illustrate the use of a washer to attach a constraint device to the sacrum S. In FIG. 4A a circular washer 402 has a central aperture 404 and a tab 406 for engagement with the constraint device. Tab 406 has an oblong aperture 408 for receiving a tether of the constraint device. A fastener such as a screw may be received in aperture 404 and threadably engaged with the sacrum S in order to secure the washer 402 to the bone. In FIG. 4B, optional recessed regions 410 are formed on either side of the spinal segment midline so that the outer surface of washer 402 will be substantially flush with the outer surface of the sacrum. Recessed regions 410 may be formed by cutting, carving, grinding, or other means known in the art and these recessed regions are also useful in helping to distribute loading more evenly along the interface between the anchor and the bone, thereby reducing the likelihood of mechanical failure. In this embodiment coatings such as hydroxyapatite or titanium may be deposited over an outer surface of the washer in order to improve fixation through osseointegration. Surface features such as beading may also be used to enhance integration of the anchor with the bone. These coatings and surface features may be used in any of the implants described in this disclosure where bone ingrowth is desirable. While a circular washer is disclosed in this embodiment, one of ordinary skill in the art will appreciate that many other geometries may be substituted, some of which may provide even better fixation of the anchor to the sacrum. FIG. 4C is a cross-section of the sacrum S showing the washer 402 disposed in a recess 410 formed in the sacrum S. A fastener 416, here a screw, is disposed through aperture 404 and threadably engaged with the sacrum S. Tether 412 has a free end 414 that is fed through aperture 408 and then fixed to itself using any of the means previously disclosed with reference to FIGS. 3A-3B. Exemplary screws which may be used include, but are not limited to those disclosed in FIGS. 17A-17B described in greater detail below. Tools which may be used to create the recessed region are also described below.

Figure 5A:
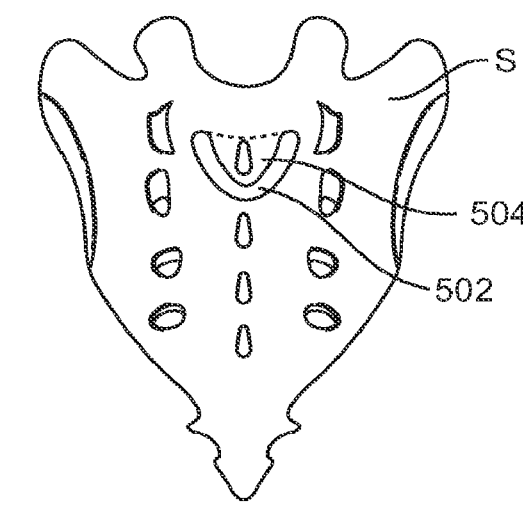
FIGS. 5A-5F illustrate use of a notched region in the
sacrum for anchoring a constraint device.
Figure 5B:
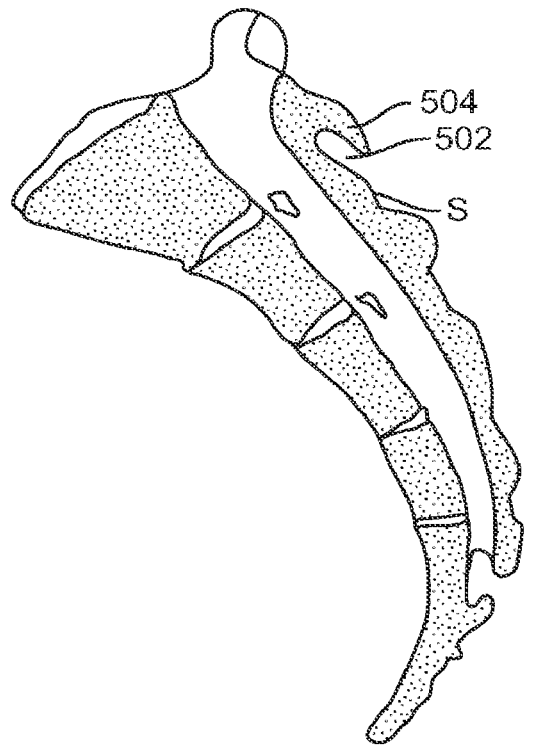
Figure 5C:
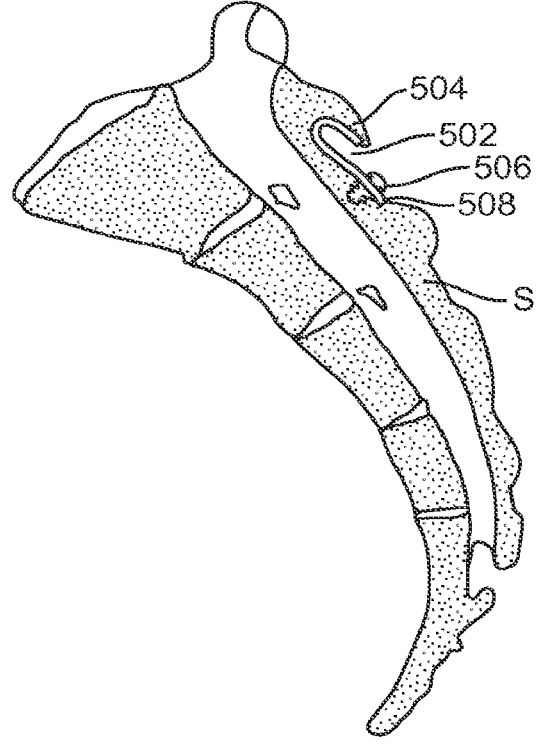
Figure 5D:
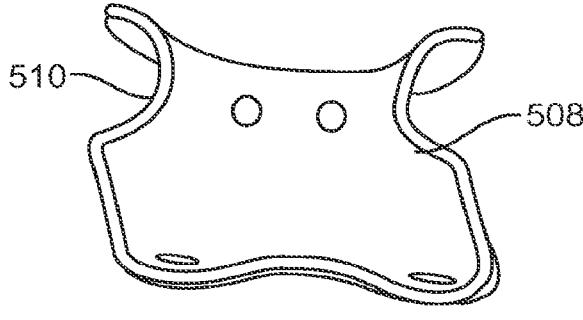
Figure 5E:
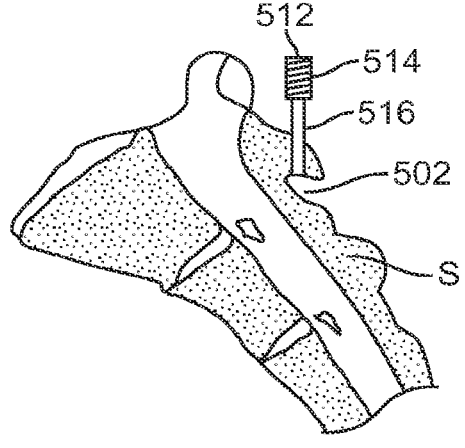

FIGS. 5A-5F illustrate how a notch may be created in the sacrum S and used to anchor a tether or a strap of a constraint device. The notch may be created in the sacral crest, a spinous process or a tubercle. In FIG. 5A a notched region 502 is formed in a crest of the sacrum S. The notch 502 lengthens the surface of engagement available for a strap if a spinous process is present but insufficient to restrain the strap, or the notch creates a raised region 504 that is similar to a naturally occurring spinous process. FIG. 5B is a side view showing notch 502 cut into the sacrum S, thereby forming the raised region 504. A tether may then be secured to the sacrum S by looping the tether directly through the notch 502 and thus no additional hardware is required. In some embodiments it is desirable to place hardware into the notch 502 in order to protect the tether/bone interface. In FIG. 5C, a plate or sheave 508 is fixed in the notch 502. The plate 508 in this embodiment is secured to the notch with a screw 506. FIG. 5D illustrates an exemplary embodiment of a plate 508 having a curved region 510 that forms a hook for engaging a tether structure. The plate or sheave 508 may be fabricated from any number of materials including metals such as stainless steel or titanium, ceramics, polymers or other biocompatible materials. One of skill in the art will appreciate that a variety of geometries may be used as a protective liner element such as the plate, sheave, or other liners described below. FIG. 5E shows how the constraint device is coupled with the notch in the sacrum S, with or without the protective sheave. In FIG. 5E, a constraint device 512 has a compliance member 514 and a tether structure 516. The tether 516 is passed through the notch 502, thereby securing the constraint device to the sacrum. An upper portion of the constraint device 512 may be coupled with a superior spinous process (not illustrated).

Figure 5F:
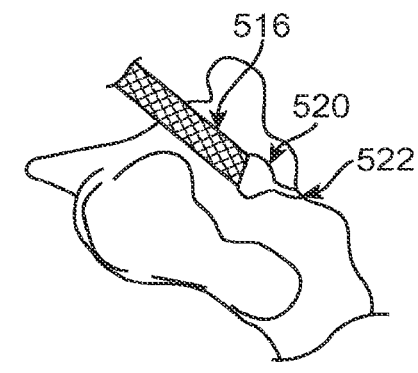

FIG. 5F illustrates an alternative embodiment of a notched sacrum used to retain the tether. In FIG. 5F a notch is created in the sacrum having a keyway which includes a narrow slotted region 522 that opens up into an enlarged aperture or slotted region 520. The narrow slotted region 522 is sized to receive the tether 516. In this exemplary embodiment, the tether is a rectangular shaped strap having upper and lower planar surfaces that represent the width of the strap and the tether also has front and back side walls generally perpendicular to the upper and lower planar surfaces that represent the strap thickness. Thus, when the tether 516 is oriented in a desired position, the tether may be advanced into the slotted region. In this embodiment, the aperture can receive the tether when the tether is advanced such that the tether leading edge is one of the side walls. This embodiment is also advantageous because when the tether structure is in tension, forces are distributed evenly along the surface of the enlarged slotted region 520. The enlarged aperture 520 may be drilled or otherwise cut in the sacrum and the narrow slotted region 522 may be cut with a saw or other bone removing tools. Additional details on tether structures and compliance members which may be applied to the embodiments disclosed in FIGS. 5A-5F or any of the tether structures or compliance members disclosed herein, are disclosed in U.S. patent application Ser. No. 12/106,103, entitled "Methods and Devices for Controlled Flexion Restriction of Spinal Segments," filed Apr. 18, 2008, the entire contents of which are incorporated herein by reference.

Figure 6:
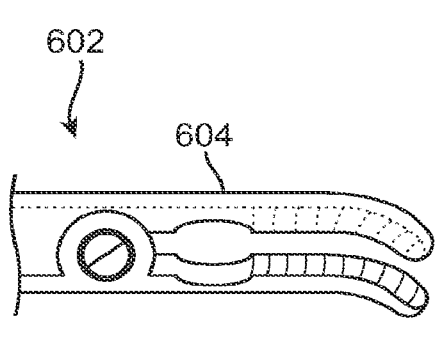
FIG. 6 illustrates an exemplary embodiment of a notching
tool.
Figure 8A:
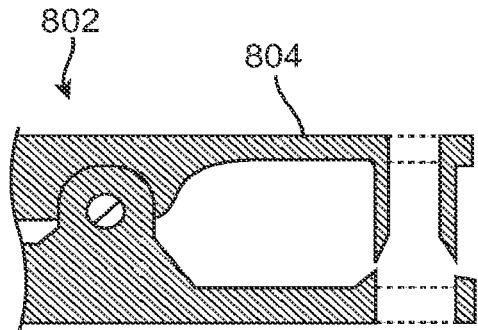
FIGS. 8A-8B illustrate an exemplary embodiment of a
punch tool.
Figure 8B:
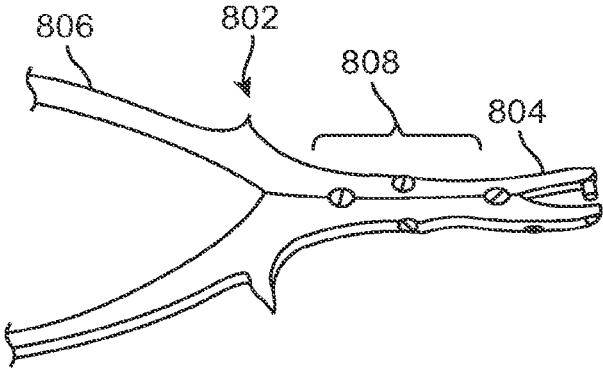
Figures 8C, 8D:
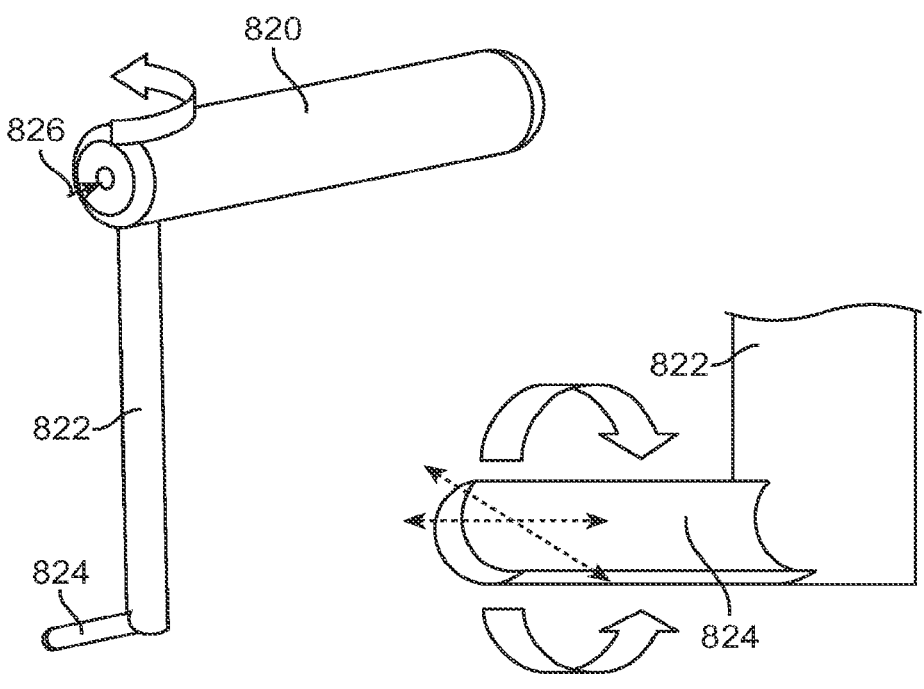
FIGS. 8C-8F illustrate additional embodiments of bone
removal tools.

Various tools and fixtures may be used to create the notch in FIGS. 5A-5F. One exemplary embodiment is illustrated in FIG. 6 and includes a forceps-like tool such as a rongeur tool 602 having a pair of jaws 604 that are adapted to remove bone and create the desired notch. The notch may also be created with files, chisels, rasps, grinders or other bone removal instruments. These instruments may be manual or power tools, such as a drill, burr or saw. FIGS. 8C-8F illustrate other embodiments of bone removal tools which may be used to create various features in the sacrum. In FIG. 8C, a crescent shaped cutting edge 824 is attached to a shaft 822 having a handle 820 for a surgeon to grasp. The crescent shaped cutting edge 824 is used to rongeur bone such as creating an undercut notch in a sacral crest which may be difficult for currently commercially available curettes. The cutting motion is a combination of both lateral and rotational movements as indicated by the arrows in FIGS. 8C-8D. The embodiment of FIG. 8C facilitates bone removal since the cutting edge 824 is offset from the shaft 822 of the tool, allowing deeper penetration into the bone as the undercut is created and preservation of midline tissues and structures. For example, it may be beneficial to create a notch, while maintaining the supraspinous ligament along the midline. An instrument that laterally accesses the bone removal site (such as those described with a cutting surface offset from the shaft) will facilitate bone removal while maintaining the midline structures. An adjustment mechanism such as a set screw 826 may be used to change the handle 820 orientation to facilitate use. FIG. 8D is an enlarged view of the cutting edge 824 in FIG. 8C.

Figures 8E, 8F:
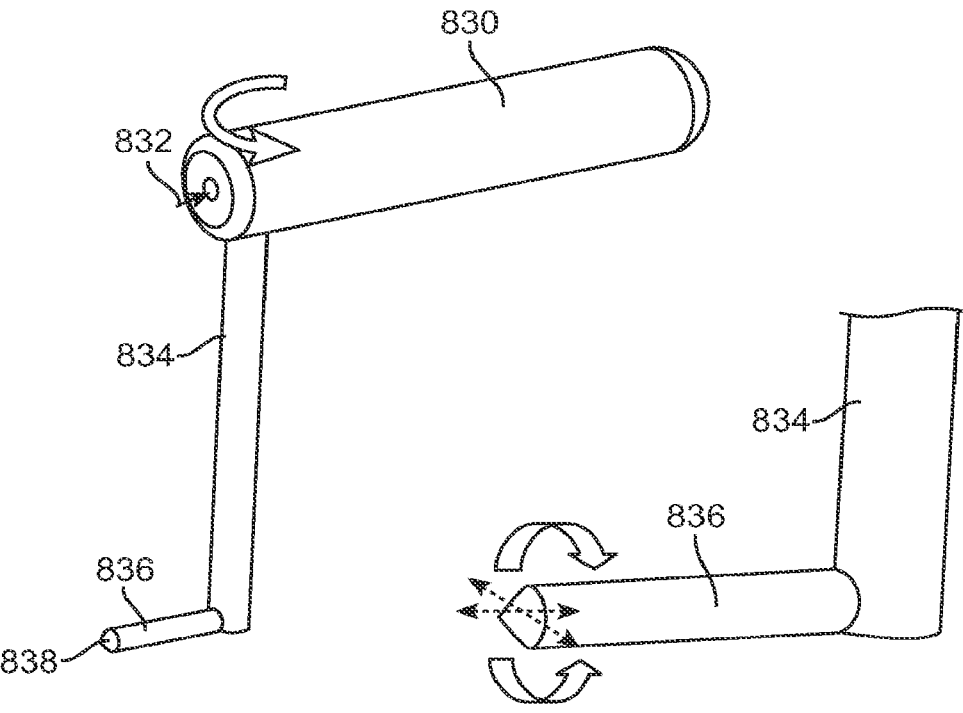

Another tool which may facilitate bone removal or creating attachment features in the sacrum is illustrated in FIGS. 8E-8F. In FIG. 8E, a curette tool has a knurled cutting surface 836 coupled to and offset from a shaft 834 having a handle 830 for grasping. An adjustment mechanism 832 such as a set screw allows adjustment of the handle position relative to the cutting edge 836. The knurled curette tool may also be used to debride bone for creating notches such as undercuts in the sacrum. A sharp tip or cutting edge 838 on the tip may be used to help the tool penetrate tissue. The knurled surface removes bone by abrading it away, similar to a file.

Figure 7A:
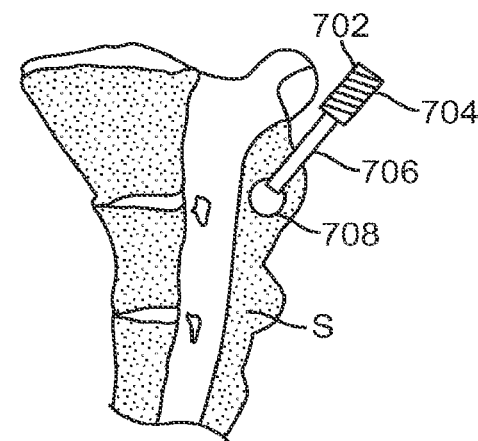
FIGS. 7A-7B illustrates use of an aperture in the sacrum
for attachment of a constraint device.
Figure 7B:
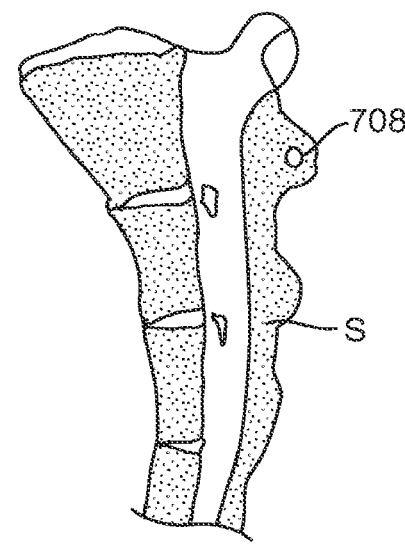

FIGS. 7A-7B illustrate an attachment method similar to that previously described with respect to FIGS. 5A-5F, with the major difference being that instead of creating a notch in a sacral crest, spinous process or tubercle of the sacrum, in this embodiment, an aperture is created in these regions of the sacrum. In FIG. 7A, an aperture 708 is created in a crest or spinous process or tubercle of the sacrum, here the aperture is a circular hole. A constraint device 702 having a tether 706 and a compliance member 704 may be coupled with the sacrum S by passing at least a portion of the tether structure 706 through the aperture 708. FIG. 7B shows a side view of the aperture 708 in the sacrum S. The aperture 708 may be drilled into the sacrum S or a punch tool may be used to create the hole. For example, in FIG. 8A, a forceps-like tool 802 similar to the rongeur tool of FIG. 6 has a pair of jaws 804 that are adapted to create the aperture. In the embodiment of FIG. 8A, the punch creates a round hole, although other shapes may also be created. FIG. 8B illustrates the forceps-like punch tool 802. The punch tool may include a handle 806 for grasping in a surgeon's hand and the jaws 804 which punch the aperture. A double-action mechanism 808 creates greater leverage in use, thereby providing higher punch forces than a single-action mechanism would. The punching jaws 804 in this embodiment could easily be substituted with the notching jaws in FIG. 6 and the tools illustrated in FIGS. 8C-8F may also be used to create the aperture.

In some embodiments where an aperture or notch has been created in a portion of the sacrum, it may be advantageous to line the aperture or notch with a protective liner element such as a bearing, liner, ferrule or grommet type of device. The liner is advantageous since it prevents direct contact between the tether and the bone thereby minimizing wear and tear on the bone or tether. Furthermore, a liner can help to more evenly distribute forces from the tether across the aperture or notch. FIGS. 18A-18B illustrate one embodiment of a liner. In FIG. 18A, aperture 1804 extends through a crest 1802 of the sacrum S. A two-piece liner is inserted into the aperture 1804. Both halves 1806 and 1808 may then be coupled together by press fitting, snap fitting, threading, bonding, welding, ratcheting mechanism, etc. to form a smooth channel 1810 through the sacral aperture 1804. The liner may have flanged ends to conform with the outer surface of the aperture 1804 and the liner may also be malleable in order to conform with the anatomy. The liner may be fabricated from many different metals such as stainless steel or titanium, as well as many different polymers. Surface treatments such as those disclosed in this specification may also be used to enhance osseo-integration of the liner with the bone. Additionally, the channel 1810 may be coated with various materials to provide desired characteristics for the tether, for example a Teflon lining may be used to provide a lubricious surface. The corners/edges of the liner may further be designed and processed to reduce friction at the points at which the tether exits the liner. FIG. 18B illustrates a perspective view of the assembled liner.

FIG. 19 illustrates an alternative embodiment of a liner or grommet. In FIG. 19, the grommet includes a main body section 1906, here a cylindrical body that is sized to fit the aperture in the sacrum. The main body 1906 also has a central channel or passage 1904 that passes through the body and accommodates the tether of the constraint device. In this embodiment, the grommet also has a number of fingers 1902 which extend from either the proximal or distal end of the grommet. These fingers are fabricated from a superelastic or shape memory alloy such as Nitinol. Therefore, the grommet may be placed in a sleeve for introduction through the sacral aperture. Once the grommet is positioned in the sacral aperture, the sleeve may be retracted and the fingers either self-expand around the edges of the aperture or self-expand upon reaching a desired temperature (e.g. above body temperature). Thus, the fingers 1902 form flanges which lock the grommet into the sacral aperture. Any of the coatings or surface treatments described herein may also be used in conjunction with this liner.

Figure 20A:
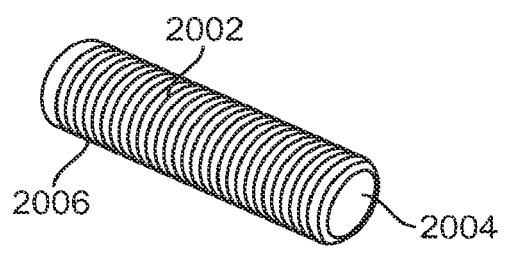
FIGS. 20A-20B illustrate another embodiment of a liner.
Figure 20B:
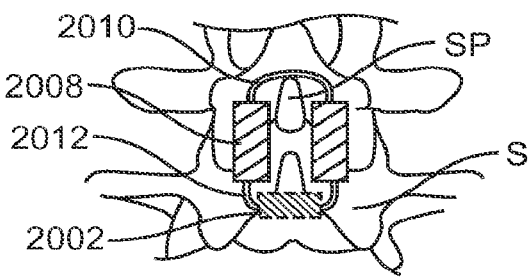

FIG. 20A illustrates a threaded liner 2002 that may be used to line apertures and notches created in portions of the sacrum. In FIG. 20A, a cylindrical tube having threads 2006 and a central channel 2004 may be threaded into the sacral aperture. The liner may be threaded into the sacral aperture and the threads allow more secure anchoring of the liner 2002 with the sacrum than other embodiments. FIG. 20B illustrates the use of the threaded liner from FIG. 20A. In FIG. 20B, a constraint device has an upper tether 2010 coupled with an upper spinous process SP and a lower tether 2012 passes through the central channel 2004 of liner 2002 that has been threaded into an aperture in the sacrum S. The liner 2002 may have any of the surface treatments or coating described herein.

Figure 21:
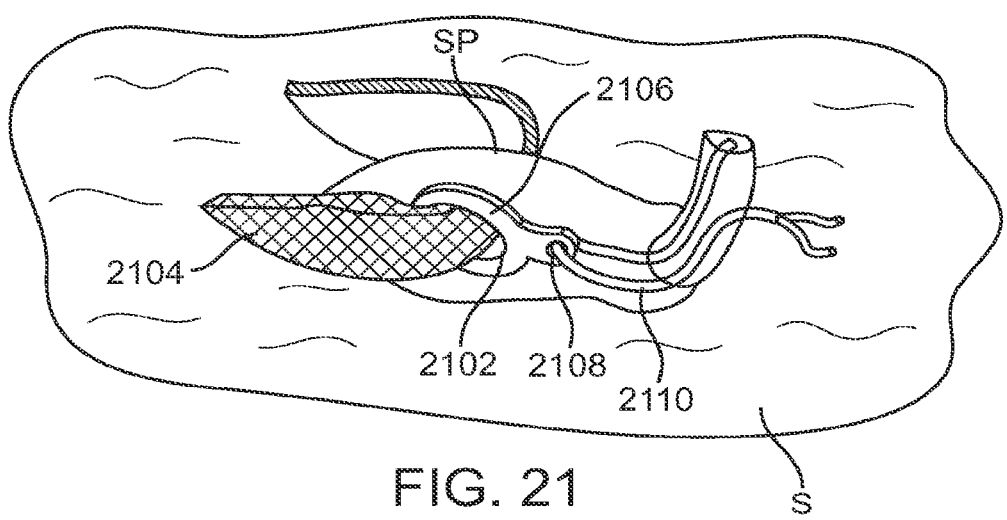
FIG. 21 illustrates a reinforcement device.

In addition to lining the internal surfaces of sacral apertures, the external surfaces of the aperture may also be reinforced. In FIG. 21, an aperture is created in a sacral crest or a spinous process or tubercle of the sacrum, and the tether structure 2104 of the constraint device is passed through the aperture. In this embodiment, one or both of the external surfaces of the sacral aperture are reinforced so that loads are not entirely borne by the bone. Here, a washer 2106 having a central opening 2102 is positioned adjacent the sacral aperture. The washer 2106 may be positioned in a groove cut into the bone similar to the embodiment described in FIGS. 4A-4C above so that it is flush with the outer surface, or the washer 2106 may be secured to the bone forming a raised region. The washer may be sutured, strapped, fixtured, buckled, tied, twisted, ratcheted or bonded to the bone. In this embodiment, the washer 2106 is held in position using a wire 2110 which passes through an aperture 2108 in the washer and the other end of the wire may be secured to the bone. External reinforcement may also be combined with internal lining. The washer 2106 may also include any of the surface treatments or coatings described in this application.

Figure 9A:
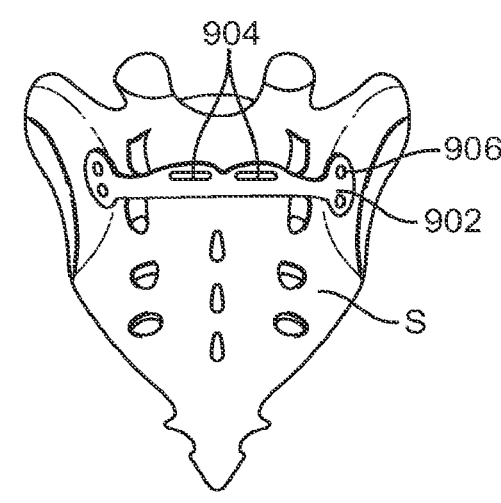
FIGS. 9A-9E illustrate various embodiments of a cross-
bar.

FIGS. 9A-9E illustrate a crossbar engaged with the sacrum as an anchor member for constraint device attachment. In FIG. 9A, a crossbar 902 is coupled with the sacrum S transverse to the midline of the spinal segment. This allows fixtures such as screws which penetrate the wings or ala of the sacrum to avoid the spinal canal and also allows the fixtures to be placed deeper into the bone for improved purchase. The crossbar 902 may have a fixed length that matches the sacral anatomy or the crossbar may have a sliding, telescoping or otherwise adjustable length. Also, the crossbar may be malleable so that it may be formed to match the surface contours of the sacrum. Fixtures such as screws 906 may be used to threadably attach the crossbar to the sacrum. In this embodiment, four screws 906 are used to secure the crossbar with the bone. Other means for attaching the anchor member to the bone may also be used in conjunction with screws or by themselves, such as using bone cement, dowel pins, etc. In FIG. 9A, the crossbar 902 has an attachment feature 904 for engaging and holding the constraint device. Here, the attachment feature comprises two slots for receiving and holding a portion of the constraint device, such as the tether. The attachment feature could include other options such as passages, hooks or retention features such as clamps, some of which are disclosed below.

Figure 9B:
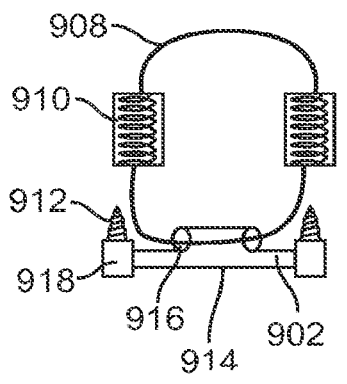
Figure 9C:
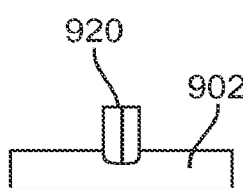

In FIG. 9B a constraint device comprises a tether 908 coupled with two compliance members 910. A lower portion of the tether 908 is advanced through an aperture 916 in a tube 914 coupled with the crossbar 902. Apertures 918 on either end of the crossbar 902 are used to receive a fastener such as a screw 912 so that the crossbar 902 is secured to the sacrum. In FIG. 9C, a post 920 is disposed on the crossbar 902 and the lower portion of the tether may then be wrapped around the post. Additional details involving the use of a post coupled either directly with the sacrum or coupled to a crossbar are described below in other exemplary embodiments.

Figure 9D:
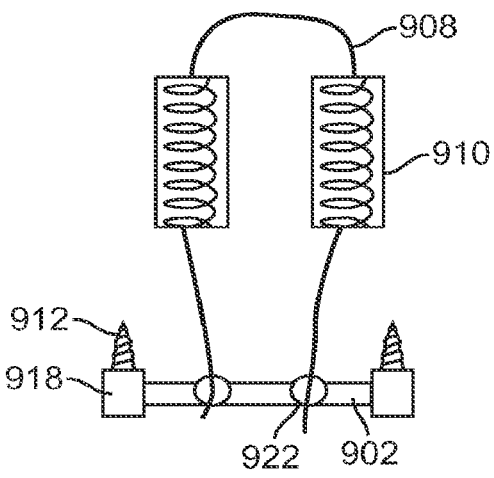
Figure 9E:
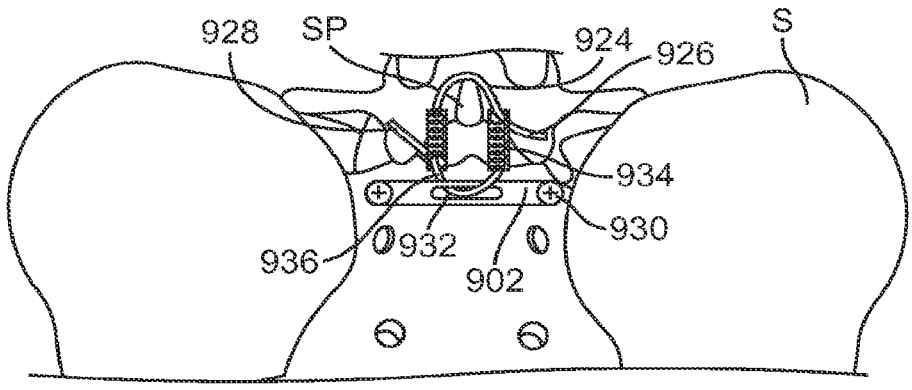

In FIG. 9D, the tether structure 908 has two free ends which may be threaded through apertures 922 in the crossbar 902. The ends may then be secured by knotting the free ends, pinning them in place, locking them, or by using other methods well known in the art. Other applicable locking mechanisms are disclosed below. In FIG. 9D, the crossbar 902 may be secured to the sacrum with screws 912 that pass through apertures 918 on either end of the crossbar. FIG. 9E illustrates another embodiment of attachment of the constraint device to the sacrum. In FIG. 9E, a crossbar 902 is fixed to the sacrum S with pins or screws 930 on either end of the crossbar 902. The crossbar 902 has an elongated, elliptically shaped aperture 932 which may receive a portion of the constraint device. In this embodiment, the constraint device comprises an upper tether 924 which is disposed around a superior surface of a superior spinous process SP. The upper tether 924 has a fixed end and a free end 926 which is engaged with a first compliance member 934. The free end 926 may be pulled through a locking mechanism on the compliance member 934, thereby adjusting length or tension in the constraint device. The fixed end is fixedly coupled with the second compliance member in this embodiment, although it also could be adjustable. A lower portion of the tether 936 also has a fixed end and a free end 928. The fixed end may be fixed with the first compliance member or it may be adjustable. The free end is similar to the upper tether free end 926, and it may be adjustably coupled with the second compliance member. The lower portion of the tether is threaded through the aperture 932, thereby securing the tether and constraint device to the sacrum S. While this method of attaching the constraint device to the sacrum is relatively easy to perform, in some situations the method may result in twisting of the constraint device which causes asymmetry in the device along with unbalanced forces applied to the spinal segment.

Figure 10:
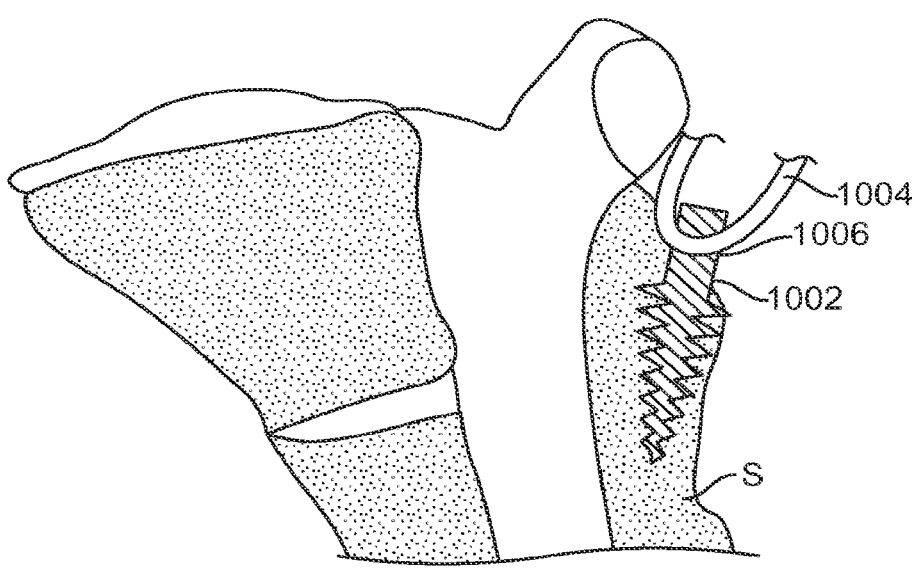
FIG. 10 illustrates use of a screw as an anchor.

FIG. 10 illustrates the use of a screw as the sacral anchor member. In FIG. 10, an anchor screw 1002 is threadably engaged with the sacrum. In this exemplary embodiment, the screw 1002 may be screwed into a crest of the sacrum axially in the caudal direction. This allows the screw to be much longer than if it were threaded perpendicularly in an anterior direction into the bone. A screw directed in the anterior direction could penetrate either the spinal canal or the anterior cortex of the sacrum and the colon. By directing the screw axially in the caudal direction permits a longer screw to be used without fear of penetrating the regions listed above, and allows a longer portion of the screw threads to be engaged with the bone, thereby providing greater purchase. A tether structure 1004 may be threaded through an aperture 1006, eyelet, hook or other attachment feature on the screw. The orientation of the screw also helps distribute loads primarily in the direction of the screw's longitudinal axis which is desirable since it results in less bending moments exerted on the screw which can cause screw fatigue, loosening and "toggling," all which are commonly associated with bone screws. In alternative embodiments, the screw may be oriented in a cranial direction.

Figure 22:
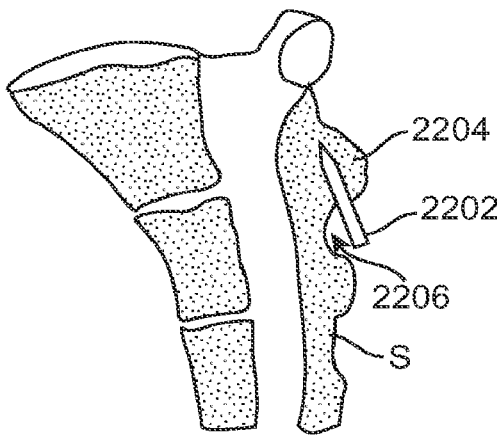
FIG. 22 illustrates the use of a retaining pin.

Instead of using a screw as in FIG. 10, a pin may be used to help create or enhance the sacral attachment region. In FIG. 22, a pin 2202 that is inserted in the cranial direction into a crest, spinous process or tubercle 2204 of the sacrum S. A portion of the pin is embedded in the bone while a portion is left unembedded. The unembedded portion of the pin forms an overhang and the tether 2206 of the constraint device is captured between the overhang and the sacrum. Thus the tether is captured on an inferior side of the sacral crest. Here, a single pin is used, although more than one pin may be used if required. In other embodiments, the pin may include a flanged rim, boss or land that prevents the pin from further penetration into the bone. The flange may be fixed or it may be adjustable so that penetration depth may be varied. Additionally, the pin may have threads on the shaft in order to facilitate implantation into the bone and enhance fixation. Still other embodiments of the pin may have an arcuate section such that as the pin is advanced into the bone, the curve forces the pin in a direction away from and prevents penetration of the pin into the sacral canal.

Figure 23A:
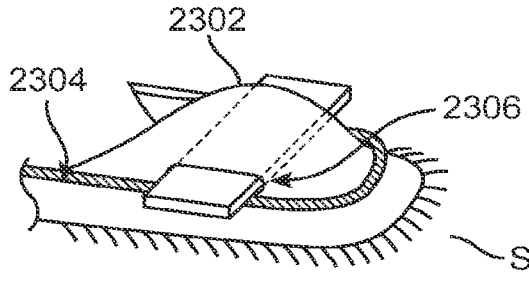
FIGS. 23A-23B illustrate retaining bar embodiments.
Figure 23B:
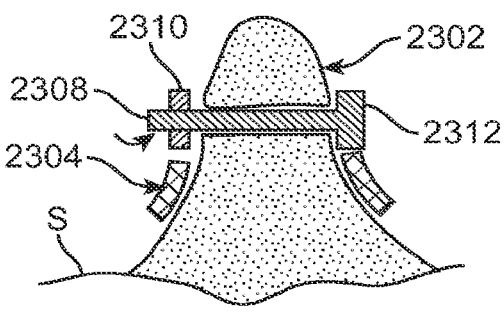

Lateral retaining bars may also be used to retain the tether to the sacrum. In FIG. 23A, a rectangular shaped retaining bar 2306 is laterally positioned in a crest, spinous process or tubercle 2302 of the sacrum S. In this embodiment, a single bar extends from one side of the crest 2302 to the other side and a portion of the retaining bar 2306 extends past each side of the crest 2303, forming a flange. Tether 2304 may then be held in position by the flanged portion of the retaining bar 2306. In FIG. 23A, the retaining bar may be a single bar pushed through the crest 2302 or two separate bars may be pressed into the crest 2302 from opposite sides. Additionally, the retaining bar 2306 may be pressed directly into the bone, or a channel may be drilled or otherwise cut into the bone before receipt of the bar. In FIG. 23B, a single retaining bar 2308 is pushed through the crest 2302. One end of the retaining bar has a T-shaped end 2312 which serves as a stop to prevent the bar from penetrating too deeply into the bone and also creates the flanged region for retaining the tether 2304. A pin, spline or other elongate element 2310 may then be placed through the opposite end of the bar in order to lock the bar into position and to create a second flanged region for retaining the tether 2304. Additionally, in other embodiments, the retaining bar ends may be curved to help enhance retention of the tether by forming hook-like regions as well as preventing sharp or long ends from protruding as well as producing a profile that may approximate the sacral surface more closely.

Figure 24A:
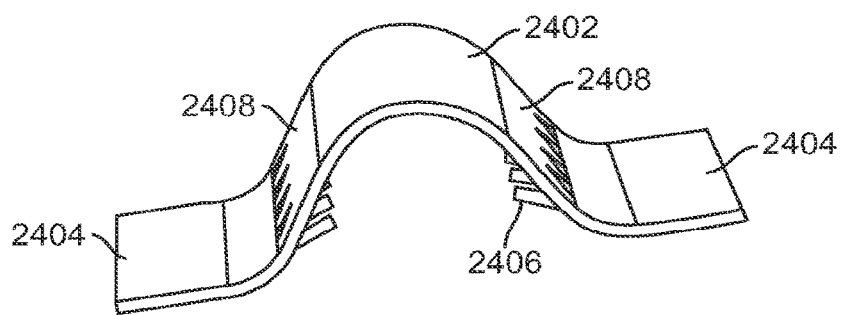
FIG. 24A-24C illustrate retaining clips.
Figures 24B, 24C:
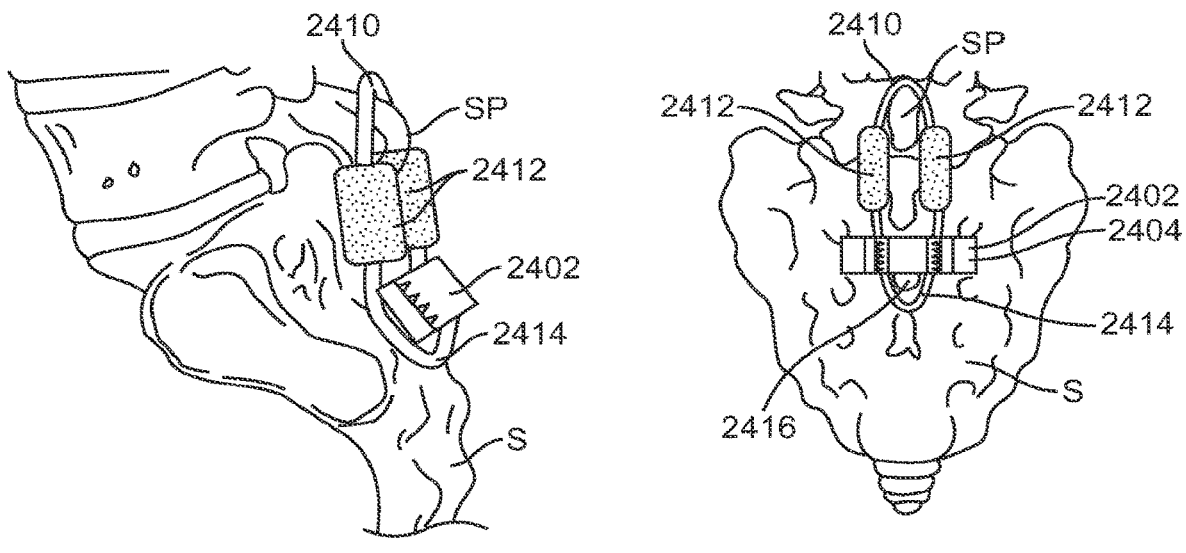

Retaining clips are also useful way of engaging a tether with the sacrum, as seen in FIGS. 24A-24C. In FIG. 24A a retaining clip 2402 has two legs 2408 and a pair of flanges 2404 or wings. Sharpened fingers 2406 help engage the clip with bone without requiring deep penetration into the bone. The fingers 2406 may comprise hooks, barbs or teeth to improve purchase on the sacral surface. In use, the clip may be stretched open and then allowed to spring back and close around a spinous process, tubercle or crest of the sacrum S. Alternatively, the clip 2402 may be pressed and deformed against these regions. In either case, the clip is then securely attached to the raised area of the sacrum S and a portion of the tether is captured under the flanges 2404 and secured to the sacrum S. FIG. 24B illustrates a side view of a constraint device having an upper tether portion 2410 coupled with a superior spinous process SP and a lower tether portion 2414 captured between the wings or flanges 2404 of the retaining clip 2402 and the sacrum S. Compliance members 2412 join the upper and lower tethers. FIG. 24C illustrates a back view of the FIG. 24B. Any of the osseo-integration surface treatments or coatings disclosed herein may also be used with retaining clip 2402 to help engagement of the clip with the bone.

Figures 25A, 25B, 25C, 25D, 25E:
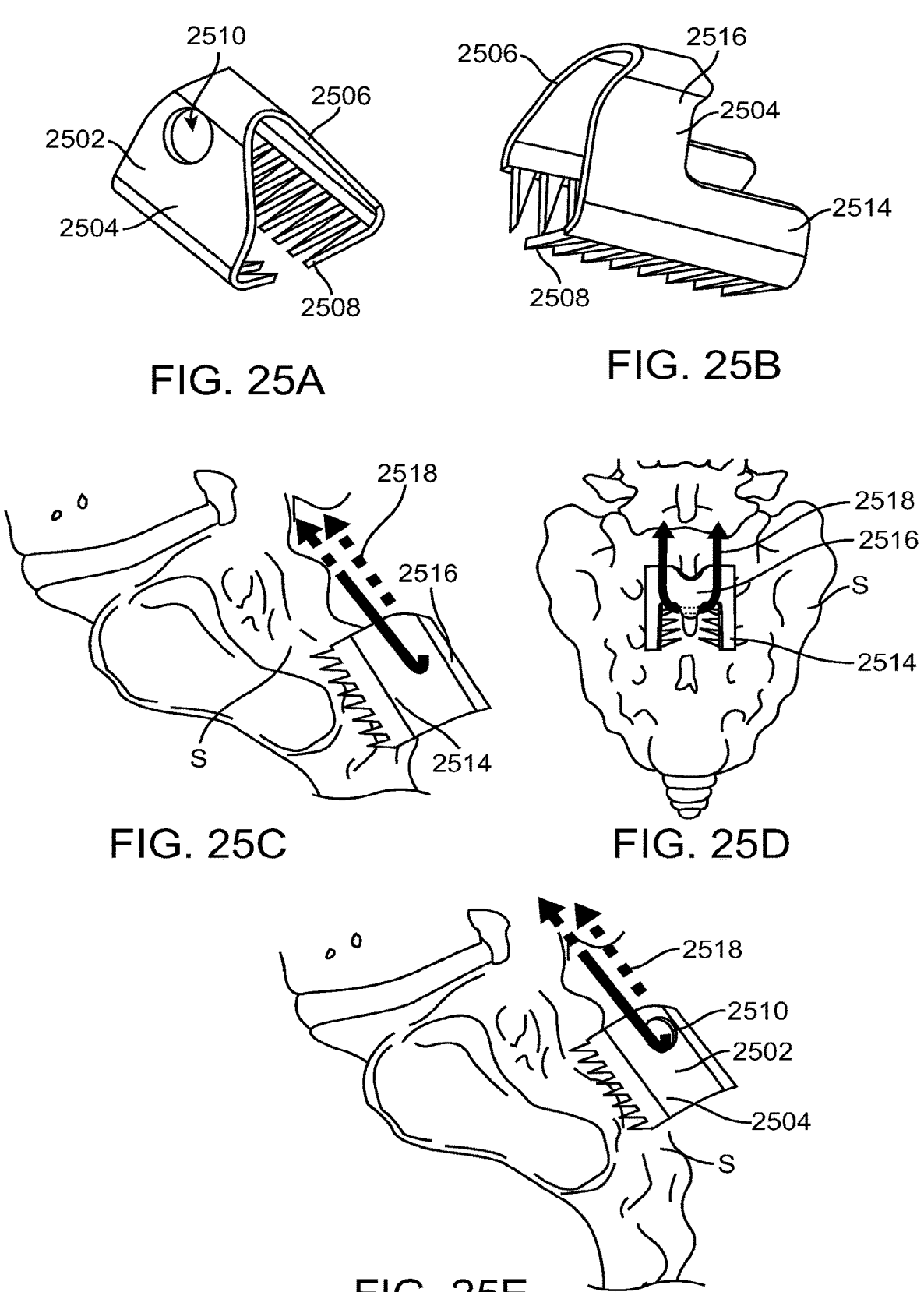
FIGS. 25A-25E illustrate additional retaining clip
embodiments.

Additional embodiments of retaining clips are illustrated in FIGS. 25A-25E. In FIG. 25A, the clip may be attached to a crest, spinous process or tubercle of a sacrum in the same manner as previously described with respect to FIGS. 24A-24C. Retaining clip 2502 has two legs 2504, 2506 which may spring into engagement with the sacrum S or which may be deformed into engagement with the sacrum S. Fingers 2508 which may take the same form as the fingers 2406 help the clip engage the bone. The retaining clip has an aperture 2510 extending through both legs 2504, 2506. The tether may be passed through this aperture, thereby securing the tether to the clip and sacrum. FIG. 25B illustrates an alternative embodiment of a retaining clip similar to that of FIG. 25A, except this embodiment does not have aperture 2510 and instead has an overhang 2516 which forms a lip for retaining the tether. FIG. 25C illustrates a side view of the retaining clip in FIG. 25B when clipped to the sacrum S and how overhang 2516 retains tether 2518. FIG. 25D is a back view of FIG. 25C. FIG. 25E is a side view showing the retaining clip of FIG. 25A when clipped to the sacrum S. Tether 2518 is secured to the clip 2504 by passing through aperture 2510. Any of these retaining clips may also include the osseo-integration coatings and surface treatments described herein to help engagement of the clip with the bone.

Figure 26A:
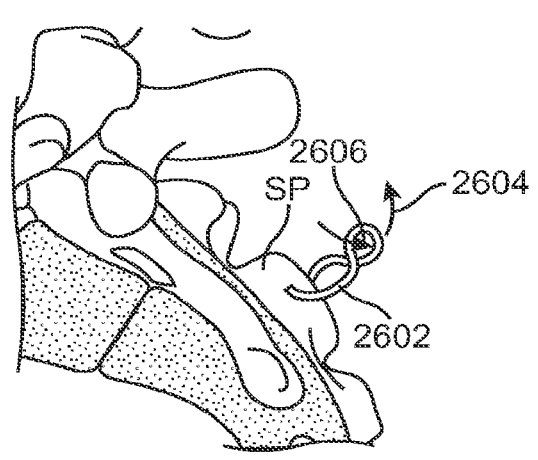
FIGS. 26A-26D illustrate still other retaining clip
embodiments.

Other clip-on anchors may include wire-like staples such as those illustrated in FIGS. 26A-26D. In FIG. 26A, a wire-like clip or staple 2602 is attached to a spinous process, tubercle or crest SP of the sacrum. The clip may be applied with a staple-like gun or the device may be applied manually by a surgeon. A tether may be coupled with the wire-like clip 2602 by passing it through a looped portion 2606 in the clip.

Figure 26B:
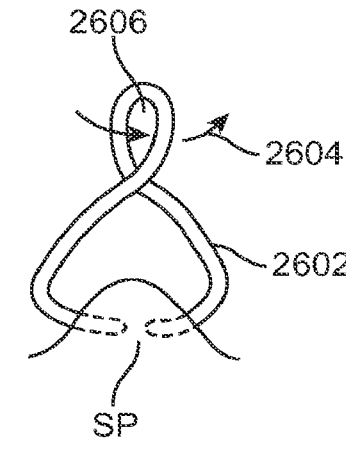
Figure 26C:
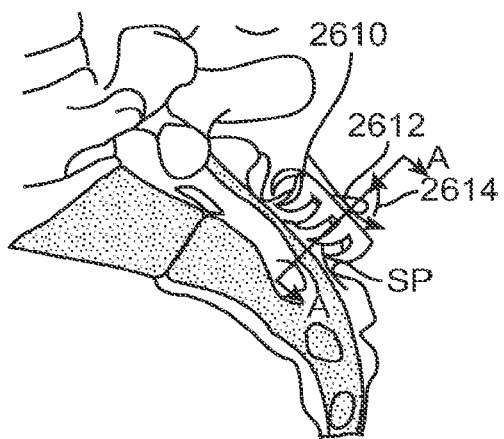
Figure 26D:
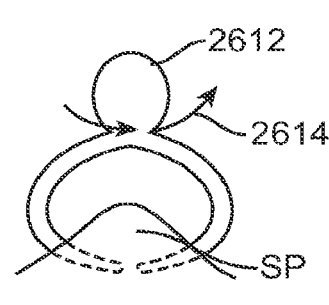

FIG. 26B is an enlarged view of FIG. 26A. The staple-type anchor may include a series of contact points such as seen in FIG. 26C. Here, the retaining clip 2610 is applied with a staple-type gun or manually by the surgeon and a hook or overhang region 2612 allows the clip to retain the tether 2614. FIG. 26D represents a cross-section of FIG. 26C taken along line A-A.

Figure 27:
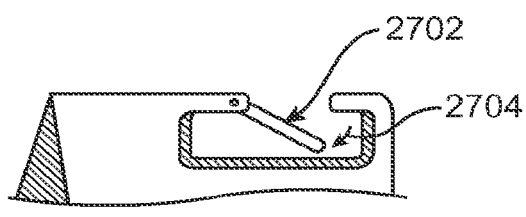
FIG. 27 illustrates a gate mechanism.

Any of the retaining clips or other devices disclosed herein may further comprise a carabiner-style gate for receiving and retaining a part of the constraint device. FIG. 27 illustrates one such embodiment. In FIG. 27, a gate 2702 is movable from a closed position to an open position. In the open position, a portion of a constraint device such as a tether may be passed into the receiver 2704. Once the gate is closed, the tether is captured by the clip. The gate may be spring loaded so that it is biased into the closed position.

Figure 28A:
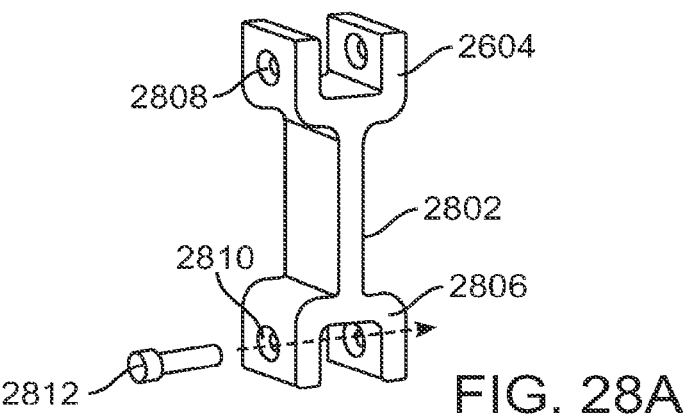
FIGS. 28A-28C illustrate a retention plate.
Figure 28B:
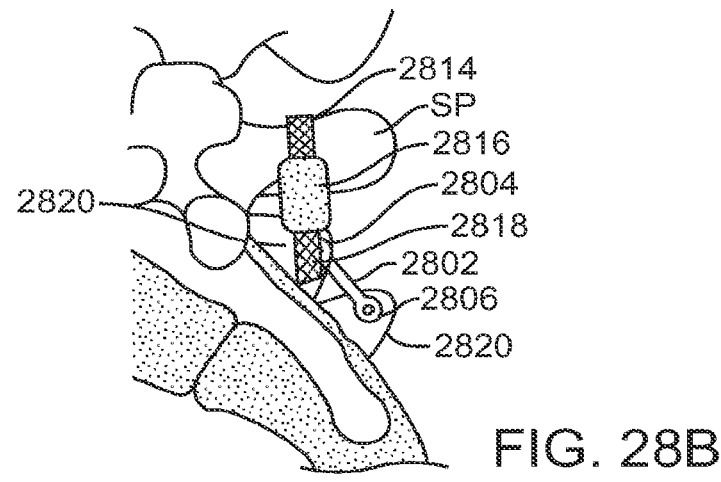
Figure 28C:
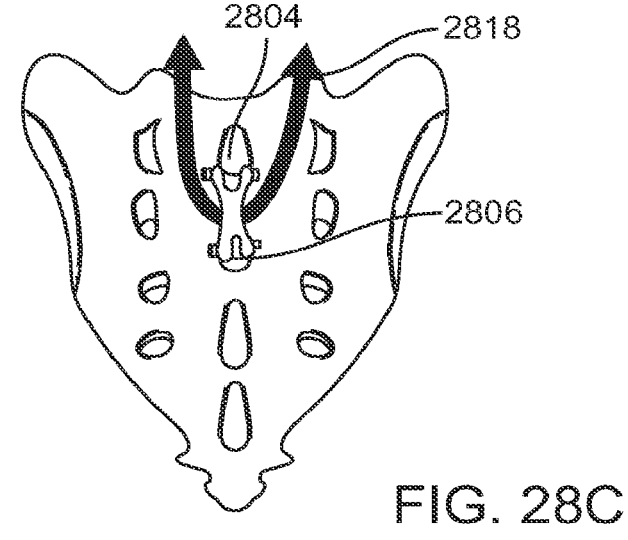

Other mechanisms for retaining a tether to the sacrum include the use of a retaining plate that is coupled to adjacent crests, spinous processes or tubercles of the sacrum. For example, in FIG. 28A, a retaining plate includes an elongate middle section 2802 having an enlarged fork-like head and tail sections 2804, 2806. Each fork-like section is U-shaped with the arms of the U forming a receptacle in which a portion of the sacrum may rest. Apertures 2808 on both head and tail sections allow a pin 2812 or other fixture to secure the retaining plate to the bone. FIG. 28B illustrates a side-view of a retaining plate 2802 coupled to the sacrum and retaining a portion of a constraint device. A constraint device has an upper tether portion 2814 coupled with a superior spinous process SP and a lower tether portion 2818 disposed and retained under the retaining plate 2802. A compliance member 2816 is coupled between the upper and lower tether portions. The retaining plate 2802 has opposite ends pinned to raised regions 2820 of the sacrum. The raised regions 2820 may be a crest, spinous process or tubercle. FIG. 28C illustrates a dorsal view of FIG. 28C.

Figure 29:
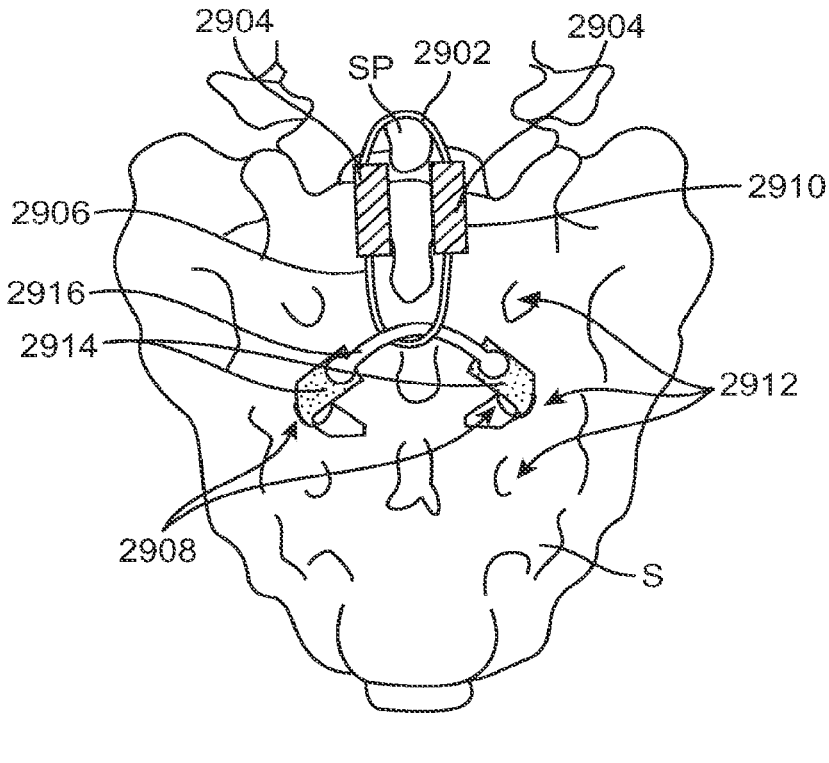
FIG. 29 illustrates a hook embodiment.

In some situations, it is preferable to use the existing natural features of the sacrum for tether anchoring rather than modifying the bone with notching or other bone removal procedures or screwing, stapling or pinning anchors into the bone. Screws in particular have many known limitations and co-morbidities such as invasiveness, blood loss, toggling or loosening of the screw, fatigue or fracture, etc. Therefore, anchors which directly appose bone without resection may be advantageous. Hooks for example are desirable since they are less invasive than screws or nails and even anchors that do penetrate bone with teeth or nails may still be preferable to screws if they require less bone resection and penetration, or are easier to implant and distribute loads more evenly or provide other beneficial features. FIG. 29 illustrates the use of hooks engaged with neural foramina of the sacrum. FIG. 29 illustrates neural foramina 2912 in the sacrum S. Neural foramina 2912 are often lateral of the spinal segment midline, therefore two foramina on opposite sides of the midline may be joined with a transverse retaining device. In FIG. 29, a retaining device includes a pair of hooks 2914 engaged in neural foramina 2908 of the sacrum S. The hooks 2914 are coupled together with a transverse member 2916 such as a bar, wire, tether or other cross member. The retaining device is used to secure a portion of a constraint device to the sacrum S and may straddle the paraspinal muscles (see FIG. 31). Constraint device 2910 includes an upper tether portion 2902 coupled with a superior spinous process SP and a lower tether portion 2906 is looped around and captured by the cross member 2916 of the retaining device 2910. A pair of compliance members 2904 couple the upper and lower tether portions 2902 and 2906 together.

Figure 30A:
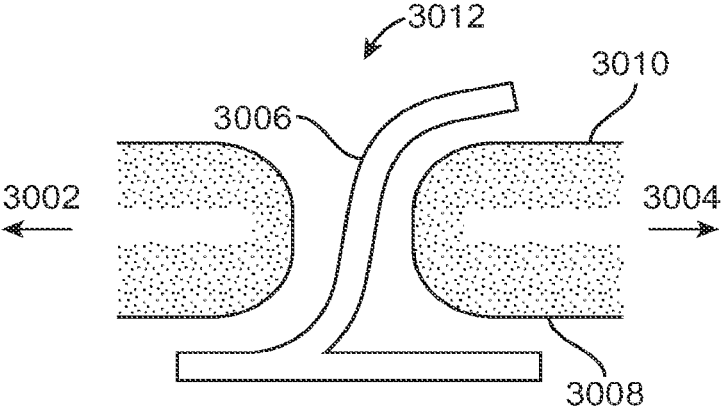
FIGS. 30A-30D illustrate the anatomy of a neural fora-
men and various embodiments of neural foramina hooks.
Figure 30B:
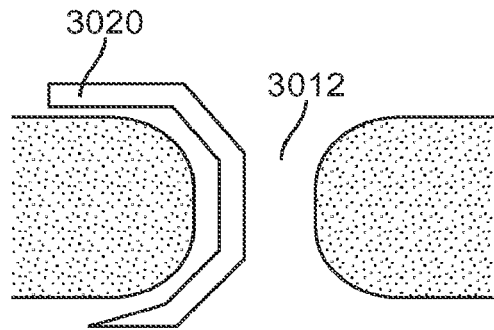
Figure 30C:
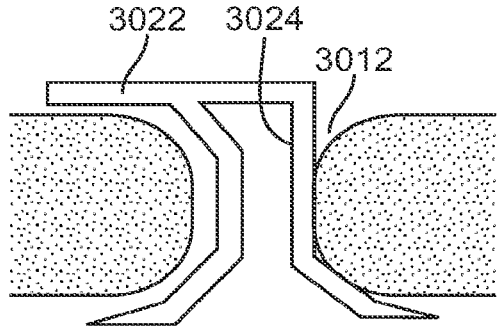
Figure 30D:
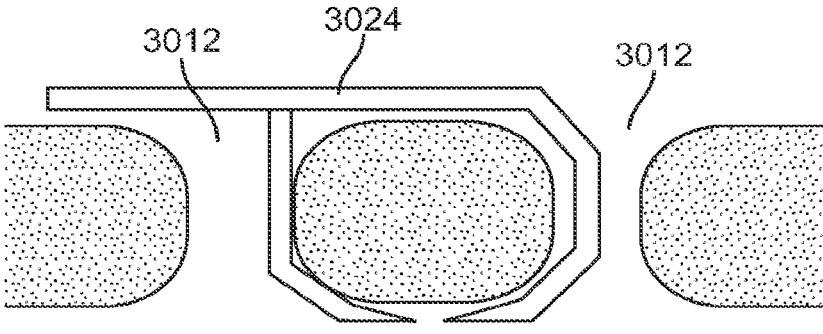

FIGS. 30A-30D illustrate the anatomy of a neural foramen and various configurations of foramenal hooks. FIG. 30A illustrates a cross section of a sacral foramen 3012. The foramen is an aperture between an upper (cranial direction 3002) and lower (caudal direction 3004) portion of the sacrum. A nerve 3006 coupled with the nerve root running in the spinal canal, near the dorsal surface of the spinal canal 3008 may exit the foramen and may run adjacent the dorsal sacral surface 3010. Because of the presence of the nerve 3006, care must be used to avoid injuring the nerve when hooks are placed in the foramen. FIGS. 30B-30D illustrate various configurations of neural foramina hooks which may be used to engage the foramen. In FIG. 30B, a hook 3020 has a single arm which is positioned in the foramen 3012 and cranially-oriented such that the hook is retained when under tension. In FIG. 30C, hook 3022 has two arms, one arm 3022 is positioned in the foramen 3012 and cranially oriented and a second arm 3024 which is positioned in the foramen 3012 and caudally oriented, thus the hook 3020 is retained in the foramen. FIG. 30D illustrates still another foramenal hook embodiment, this embodiment includes a hook 3024 having a claw configuration with the claw positioned in adjacent foramen so that the claw grasps the bone in between the two foramina. Thus, in FIG. 30D, the hook remains engaged with the sacrum.

Figure 31:
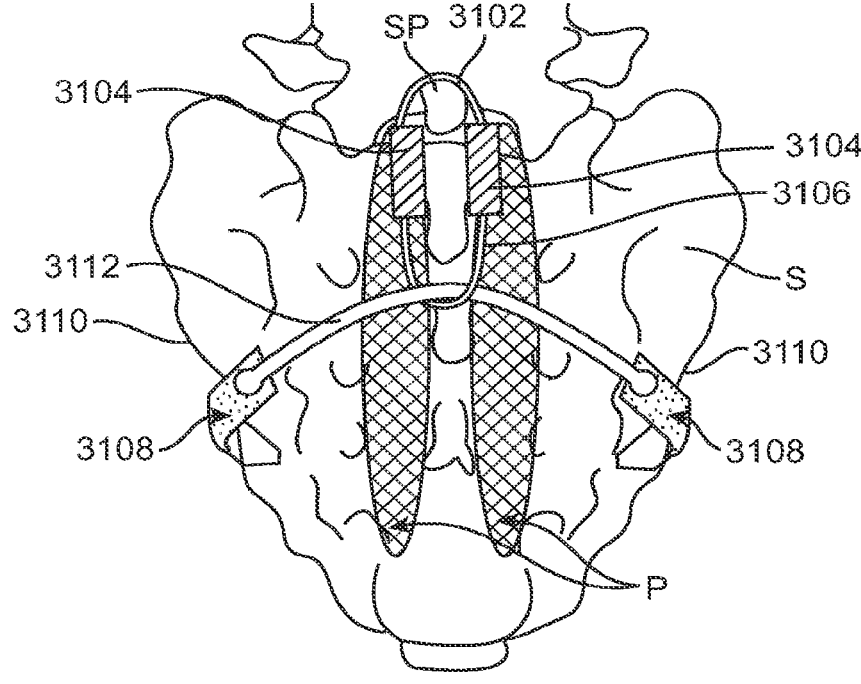
FIG. 31 illustrates additional embodiments of sacral
hooks.

The foramina hooks previously described have many advantages, but must be used with caution in order to avoid pinching the nerves in the area. Therefore, in some situations, it still may be advantageous to use hooks, but to engage them with another portion of the sacrum that minimizes or avoids pinching nerves. FIG. 31 illustrates a retaining device having a pair of hooks 3108 that are engaged with a lateral edge 3110 of the sacrum S. A transverse connector such as bar, rod, wire, tether or other cross member 3112 joins the two hooks 3108 together. A lower tether portion 3106 of the constraint device may then be looped around the cross member 3112 and secured to the sacrum S. The remainder of the constraint device includes an upper tether portion 3102 engaged with a superior spinous process SP and a pair of compliance members 3104 joining the upper and lower tether portions together. In addition to avoiding the nerves in the foramina, this embodiment also allows the retaining device to straddle the paraspinal muscles P thereby causing minimal disruption to the muscles. Any of the hook embodiments previously described may be used to hold the retaining device to the edges of the sacrum.

Figure 11A:
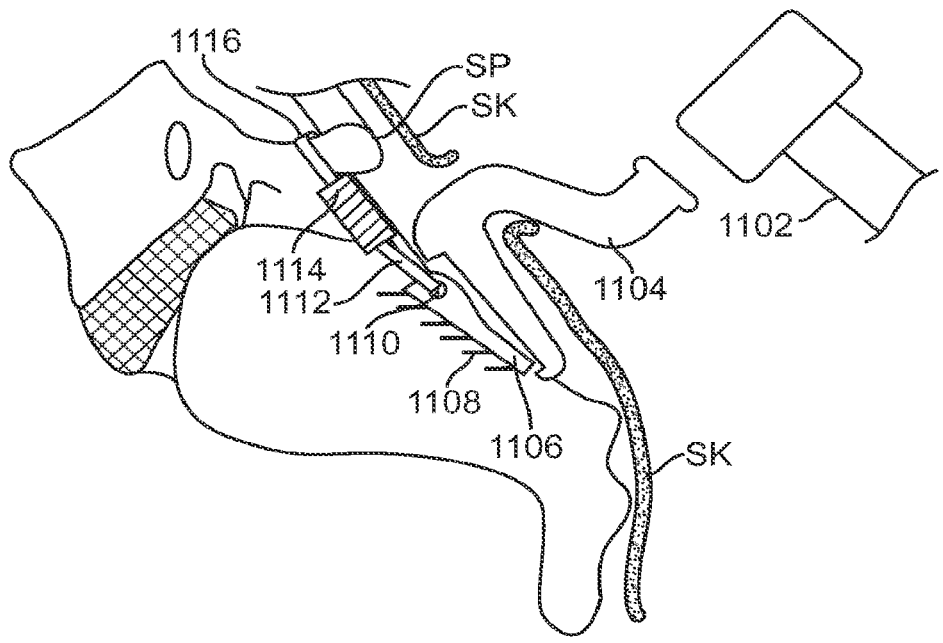
FIGS. 11A-11D illustrate an anchor coupled with the
sacrum.

An anchor member may be attached to the sacrum without screws as seen in FIGS. 11A-11D. In FIG. 11A, an anchor plate 1106 having a plurality of nail-like protrusions 1108 is engaged with the sacrum S. In this embodiment, the nails are inclined relative to the outer surface of the plate 1106 to help resist applied loads from the constraint device which includes an upper tether portion 1116 coupled with a superior spinous process SP and a lower tether portion 1112 coupled with the anchor plate 1106 via an aperture 1110. In other embodiments, the anchor plate 1106 may have a plurality of apertures through which individual nails may be passed. Using a plurality of nails distributed along the length of the anchor allows loads to be distributed over more points therefore shorter nails may be used, avoiding the need for deep penetrating nails. Preferably, the nails only penetrate the cortical bone on the dorsal surface of the sacrum, minimizing the risk of neural injury, but penetration may be varied as required. A compliance member 1114 is disposed between the upper 1116 and lower 1112 portions of the tether. In this exemplary embodiment, the anchor plate 1106 may be inserted through a minimally invasive incision through the skin SK and then hammered into position with a custom placement tool 1104 and mallet 1102. In this embodiment, the aperture 1110 allows coupling of the anchor plate 1106 with the tether, although other attachment features such as a hook may be used. One of the advantages of this type of anchor is that there is greater flexibility in attachment of the tether structure in the cranial or caudal direction. Attaching the tether structure to native anatomy such as a spinous process or a notch in the sacrum is likely to be limited to specific areas of the sacrum. Using the anchor plate allows the attachment region to be moved in the cranial or caudal direction which will help accommodate the compliance member and other portions of the tether structure.

Figure 11B:
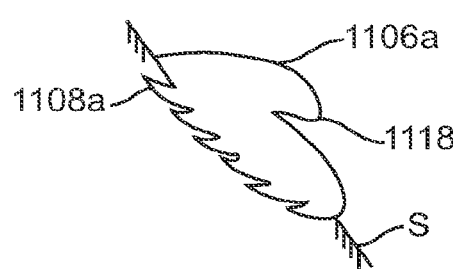
Figure 11C:
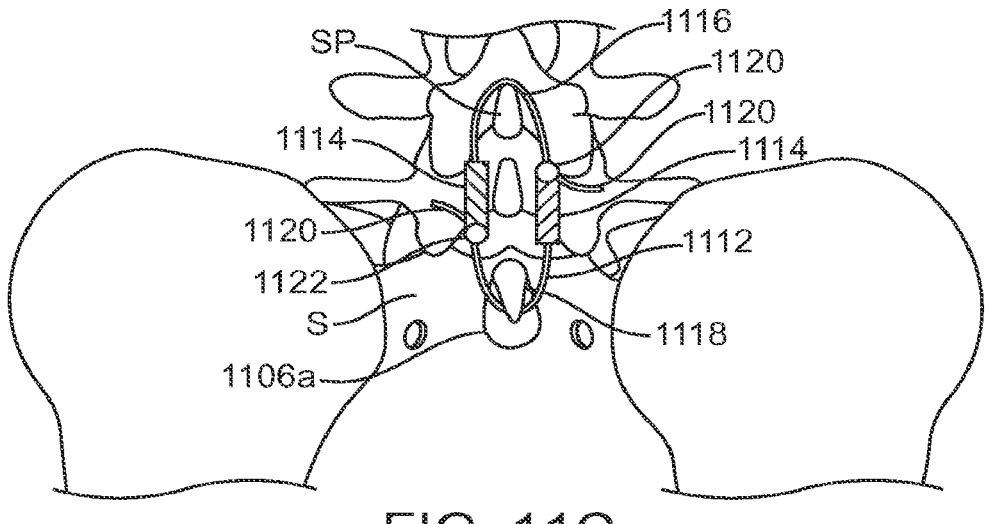
Figure 11D:
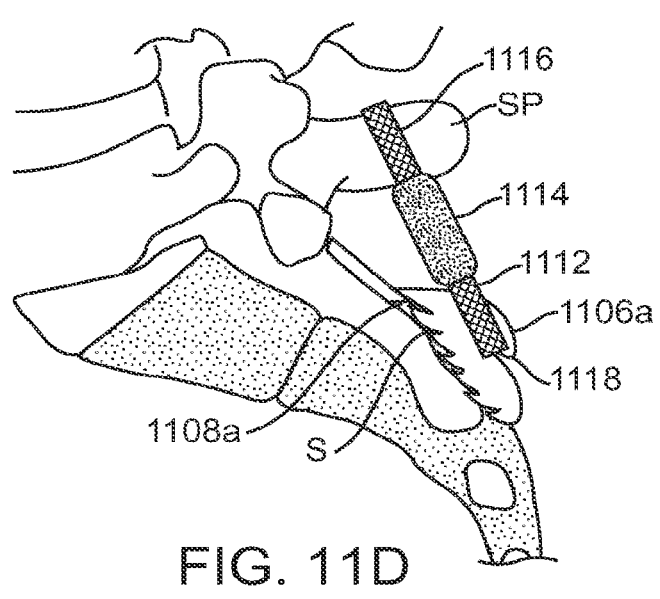

An alternative embodiment of the anchor plate 1106 may be seen in FIG. 11B. In FIG. 11B anchor plate 1106a comprises a hook 1118 for engaging the tether structure and instead of nails, a plurality of hooks, claws or barbs 1108a are used to secure the anchor plate 1106a to the sacrum S. FIG. 11C shows a constraint device having an upper tether portion 1116 coupled with a superior spinous process SP and a lower tether portion 1112 coupled with the hook 1118 on anchor plate 1106a. A free end 1120 of the upper tether 1116 and a free end 1120 of the lower tether 1112 pass through a locking mechanism 1122 adjacent each compliance member 1114. Thus, length or tension in the tethers may be adjusted. Additional details on the locking mechanism are disclosed elsewhere in this application. FIG. 11D shows a side view of the constraint device coupled with a spinous process SP and the anchor plate 1106a.

Additionally, the surfaces of anchor plate 1106 that engage the sacrum S may be treated to create a surface that promotes osseointegration of the plate with the bone. Exemplary treatments include beading as well as hydroxyapatite and titanium coatings. These surface treatments may be applied to any of the implants disclosed in this specification.

Figure 12:
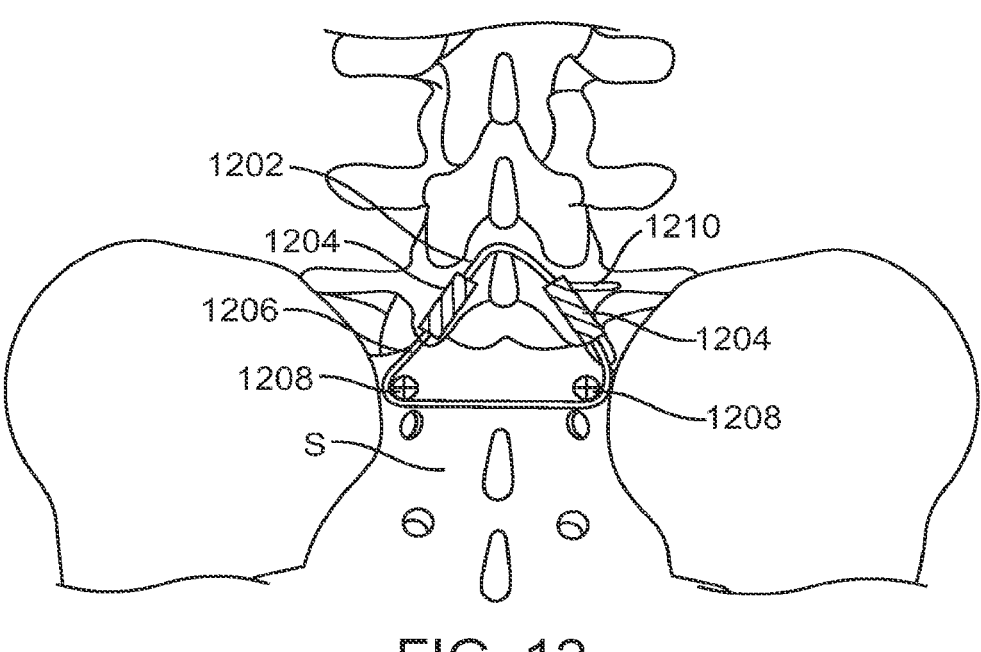
FIG. 12 illustrates use of a screw or pin as an anchor.

Referring now to FIG. 12, pins or screws 1208 are placed in the sacrum S and help to secure a constraint device to the bone. In FIG. 12, a constraint device includes an upper tether portion 1202 that is disposed over a superior spinous process and a lower tether portion 1206 is disposed around two screws 1208 threaded into the sacrum S. Two compliance members 1204 join the upper and lower tether portions together. Additionally, a free end 1210 of the upper tether portion 1202 is received by one of the compliance members 1204 and allows adjustment of the tension or length in the constraint device.

Figure 13:
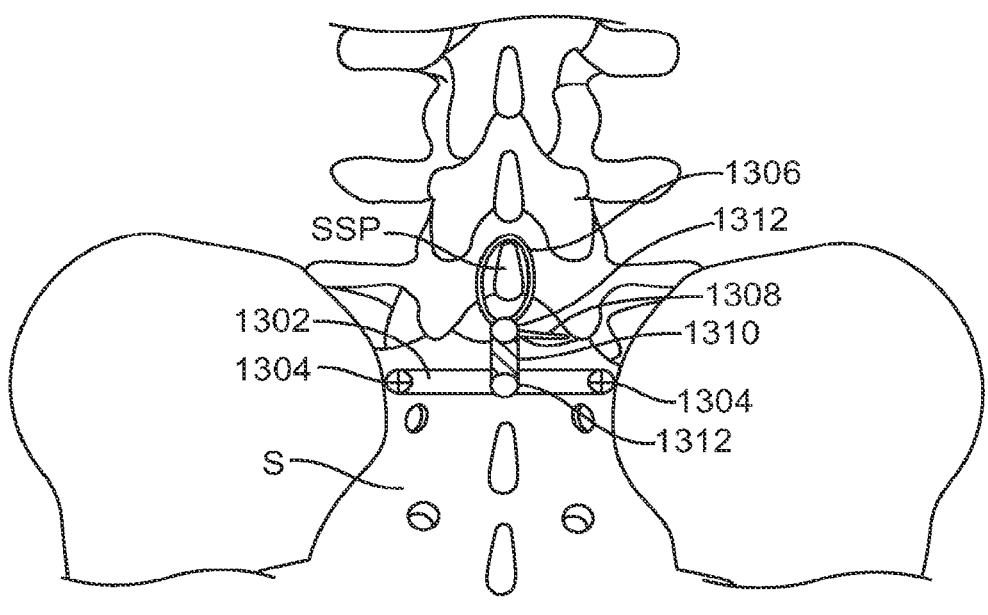
FIG. 13 illustrates another embodiment of a screw or pin
as the anchor.

In FIG. 13 a crossbar 1302 is anchored to the sacrum S with two screws 1304 on either end of the crossbar 1302. In this embodiment, the constraint device includes an upper tether 1306 looped around a superior spinous process SSP with a free end 1308 engaged with a locking mechanism 1312 on the compliance member 1310. The locking mechanism allows the length and tension of the constraint device to be adjusted to accommodate different patients. Various locking mechanisms are disclosed in U.S. patent application Ser. No. 12/479,016 and PCT Publication No. WO 2009/149407, the entire contents of both are incorporated herein by reference. Also in this embodiment, a lower portion of compliance member 1310 is coupled with a post or raised screw 1312 disposed on the crossbar 1302. The raised screw 1312 is preferably located along the spinal segment midline, although it may be located off center if desired.

Figure 14A:
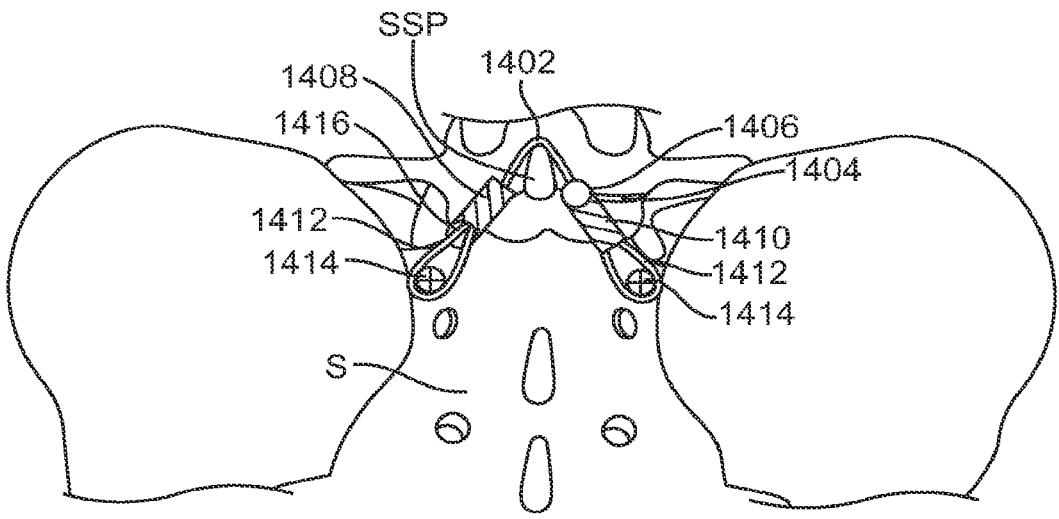
FIGS. 14A-14B illustrate still other embodiments of a
screw or pin as the anchor.
Figure 14B:
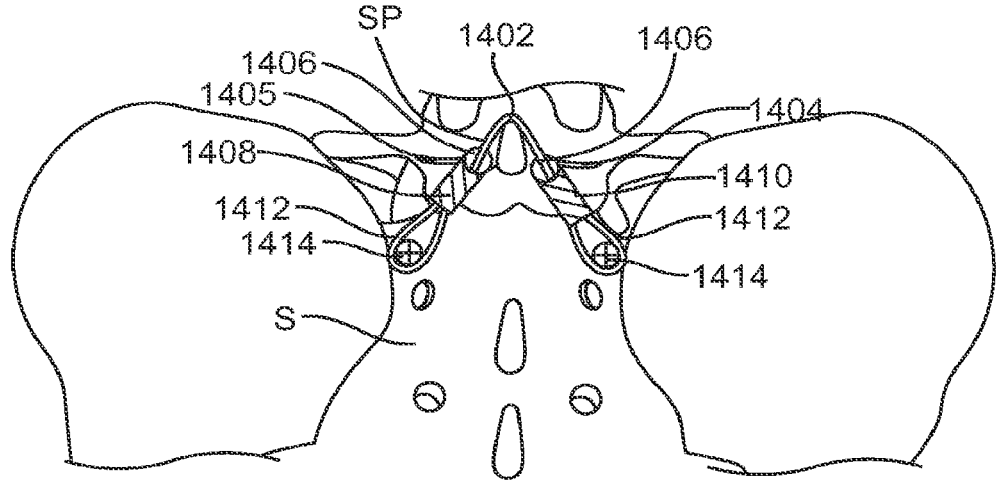

FIGS. 14A-14B illustrate embodiments of constraint devices anchored to the sacrum S with a pin or screw. In FIG. 14A, a constraint device includes an upper tether 1402 disposed at least partially around a superior surface of a superior spinous process SP. One end of the upper tether 1402 is pre-attached to a first compliance member 1408 while the opposite end of tether 1402 is a free end 1404 that is received in a locking mechanism 1406 of a second compliance member 1410. The locking mechanism 1406 allows length and/or tension in the constraint device to be adjusted. Any of the locking mechanisms previously described above may be used in this embodiment. The first compliance member 1408 is coupled to a loop 1412 in the tether structure and the loop 1412 is secured to a post or screw 1414 in the sacrum S. An optional adjusting mechanism 1416 may be included in the first compliance member 1408 or the second compliance member 1410 in order to allow further adjustment of length and/or tension in the constraint device. A second loop 1412 is coupled with the second compliance member 1410 and a pin or screw 1414 secures the second loop 1412 to the sacrum S.

The embodiment of FIG. 14B is similar to that in FIG. 14A with the major difference being that the tether structure in FIG. 14B has two free ends that may be adjusted. In FIG. 14B, the constraint device includes an upper tether 1402 disposed at least partially around a superior surface of a superior spinous process SP. Both free ends 1404, 1405 of the upper tether are received in a locking mechanism 1406 in each of the two compliance members 1408, 1410. The locking mechanism 1406 may be any of those previously disclosed above. Similar to the embodiment of FIG. 14A, looped ends 1412 of the tether are coupled on one end to a compliance member, either 1408, 1410 and secured at the other end to a pin or screw 1414 in the sacrum S. In alternative embodiments the looped ends 1412 may be coupled to one notch or aperture in the sacrum (similar to FIGS. 5E, 5F or 7A), or in still other embodiments the looped ends are individually coupled to a notch or aperture, one on each side of the spinal segment midline.

The embodiments of FIGS. 15A-15E use a pin or post secured to a sacral crossbar as an attachment point for the constraint device. In FIG. 15A, a crossbar 1522 is secured to the sacrum S with two screws 1512 on either end of the crossbar. A central pin or post 1516 is coupled with the crossbar 1522 and is used to attach a constraint device to the sacrum. The constraint device in FIG. 15A includes an upper tether 1502 disposed around an upper surface of a superior spinous process SP. A free end 1506 of the upper tether 1502 is received in a locking mechanism 1504 of a first compliance member 1508 so that tension and/or length may be adjusted. The opposite end of upper tether 1502 is pre-attached with a second compliance member 1508. A lower tether 1514 is disposed around a central pin or post 1516 and includes a free end 1510 that is also received in a locking mechanism 1520 of the second compliance member 1508 to allow additional adjustment of length and/or tension in the constraint device. The opposite end of the lower tether 1514 is pre-attached with the first compliance member. FIG. 15B illustrates the central pin or post 1516 in greater detail. The post 1516 comprises a central concave region 1520 disposed between two enlarged shoulder or head regions 1518. This helps prevent the tether 1514 from sliding off the post.

The embodiment of FIGS. 15C-15D is similar to the embodiment illustrated in FIGS. 15A-15B with the major difference being how the compliance device is coupled to a central post. As in FIG. 15A, a crossbar 1522 is secured to the sacrum S with two screws 1512 on either end of the crossbar 1522. The constraint device in this embodiment generally takes the same form as the device described with respect to FIG. 15A. In FIG. 15C, central post 1513 has an aperture and the lower tether 1514 may be advanced through this aperture and then secured to the compliance members 1508. FIG. 15D illustrates the central post 1513 in greater detail. The aperture may be elliptical or rectangular or any other shape that may receive the tether structure 1514. An additional lower aperture 1526 allows the central post 1513 to engage the crossbar 1522 and a set screw 1530 may be used to secure the components together.

Figure 16A:
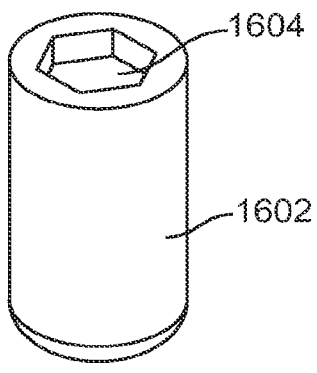
FIGS. 16A-16F illustrate various embodiments of pins or
posts that may be used as the anchor.
Figure 16B:
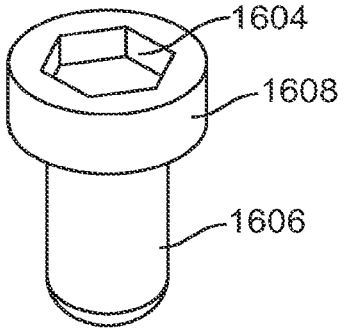
Figure 16C:
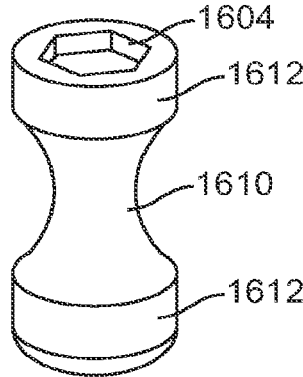

Various embodiments of posts or pins are illustrated in FIGS. 16A-16F. Any of these may be fabricated from metals such as titanium or stainless steel, or they may be made from other materials such as polymers or ceramics. Additionally, any of these may be used in any of the embodiments disclosed above where the constraint device is either wrapped around a post, pin, or screw or threaded through an aperture in the post, pin, or screw. These posts or pins may be secured directly into the sacrum or to an anchor member such as a crossbar that is secured to the sacrum. The posts/pins may be press fit into engagement with the sacrum or the anchor member, or they may be coupled with another fastener such as a screw that is threadably engaged with the bone or anchor. Referring now to FIG. 16A, a pin has a elongate cylindrically shaped body 1602 having a substantially constant diameter. A hex head 1604 is provided so that a tool may engage and rotate the pin. One of skill in the art will appreciate that other heads such as a slot, Phillips, Torx, etc. may easily be substituted for the hex head in this embodiment as well as any of the screw, pin or post embodiments disclosed herein. In FIG. 16B, the pin has an elongate cylindrical body 1606 also with a constant diameter, except that this embodiment also includes an enlarged head/shoulder region 1608 that is coupled with the cylindrical body 1606 in order to prevent a tether from slipping off the post. This embodiment also includes a hex head 1604. The embodiment of FIG. 16C includes a concave central region 1610 disposed between two enlarged head/shoulder regions 1612, one of which includes a hex head 1604. Again, the enlarged regions help prevent slipping of a tether off the post.

Figure 16D:
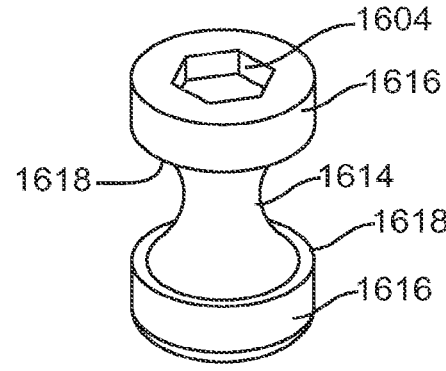
Figure 16E:
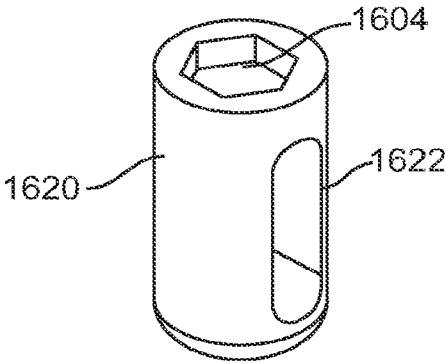
Figure 16F:
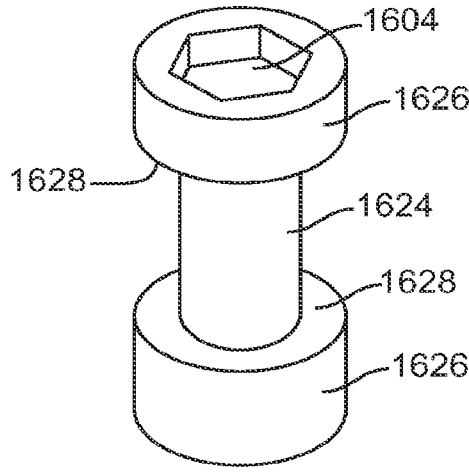

FIG. 16D illustrates yet another embodiment of a pin or post that may be used to help secure a constraint device either directly or indirectly with a sacrum. In FIG. 16D, the central region of the pin is concave and it is surrounded on either side by an enlarged head/shoulder region 1616. One end of the post includes a hex head 1604. The transition from the concave region to the enlarged head/shoulder region includes an annular flange 1618 on both ends and this feature is also helpful for preventing slippage of the tether structure off the pin/post. In FIG. 16E, the pin/post has a cylindrical body 1620 with a central slot 1622 or aperture for receiving the tether structure. Often, one end of the tether is free so that it may be threaded through the slot and then secured to the remainder of the constraint device with a locking mechanism. Once the tether is fed through the slot, it is captured and cannot slip off the post. In this embodiment, the slot is elliptical in shape, although one of skill in the art will appreciate that other slot geometries may also be used. FIG. 16F illustrates still another embodiment of a post/pin. In this embodiment, a central cylindrically shaped region of constant diameter 1624 is surrounded on either side by an enlarged head/should region 1626. The transition from the central cylindrical region 1624 to the enlarged head regions 1626 includes a step or flanged region 1628 on both ends.

Figure 17A:
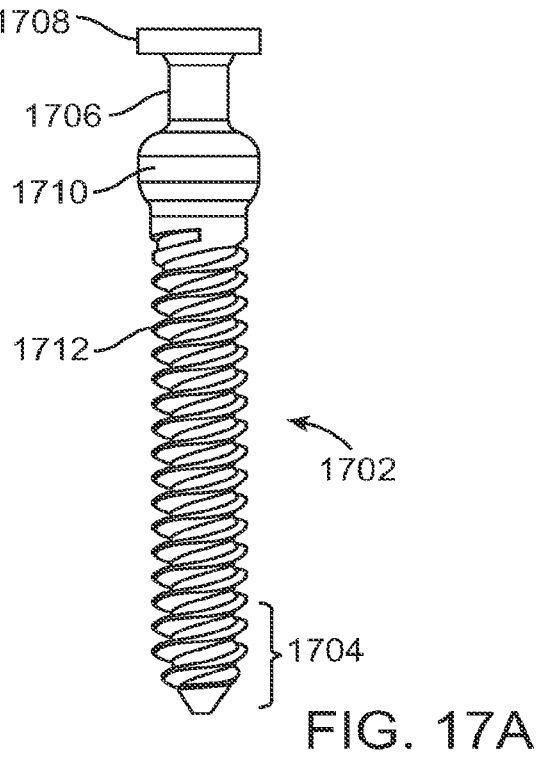
FIGS. 17A-17B illustrate two exemplary embodiments of
screws that may be used as the anchor.
Figure 17B:
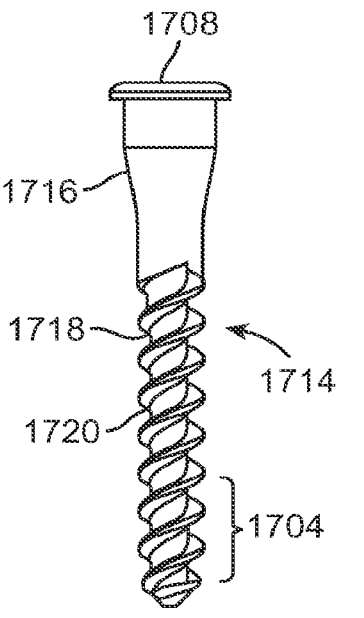

As previously mentioned, any of the post/pin embodiments may be coupled with a screw for direct engagement with the sacrum. FIGS. 17A-17B illustrate two exemplary embodiments of post/pins having threaded regions that may be threadably engaged with the sacrum. In FIG. 17A, a screw 1702 includes a head region having a recessed step 1706 for holding a tether. A flange region 1708 prevents the tether from slipping off the post. A hex head or other driver feature may be included on a top surface of the flange region. A tapered head region 1710 allows better grip with cortical bone and a tapered thread 1712 increases the grip of the screw with bone. The dual lead 1704 design is also desirable since it allows faster and more efficient penetration of the screw into the bone. FIG. 17B illustrates an alternative embodiment of a screw 1714 that can be threaded into the sacrum. In FIG. 17B, flanged region 1708 prevents slippage of the tether off the pin and provides an area for a driver feature such as a hex head. An increased thread pitch 1718, dual lead 1704 and deeper thread 1720 permit more efficient cutting into the bone. This embodiment also includes a tapered head 1716. Exemplary dimensions of these screws may include an outer diameter from about 5 mm to about 8 mm, and more preferably from about 6.5 mm to about 7.5 mm, with a thread length ranging from about 20 mm to about 70 mm and more preferably from about 35 mm to about 50 mm.

Figure 32:
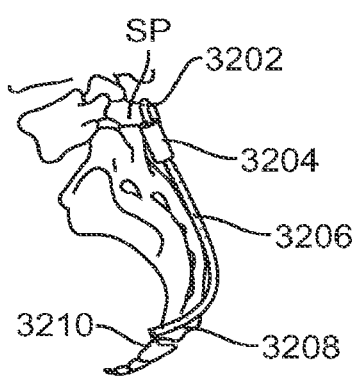
FIG. 32 illustrates attachment of a constraint device with
the coccyx.

Many embodiments disclosed above relate to attachment of a constraint device to the upper sacrum. An alternative attachment location could be the lower sacrum such as the coccyx or sacro-coccygeal junction. For example, in FIG. 32, a constraint device has an upper tether portion 3202 coupled to a superior spinous process SP and a long lower tether portion 3208 that passes over the sacrum and is coupled to the coccyx 3210. A pair of compliance members 3204 (only one illustrated in this side view) join the upper and lower tether portions. This configuration is desirable since the lower tether portion cannot slip off. Additionally, the tethers are oriented parallel to the spinal midline and medially oriented close to the midline which are preferred positions for a flexion restricting device. Various embodiments of constraint devices which may be coupled with the lower sacrum are illustrated in FIGS. 33A-33B.

Figure 33A:
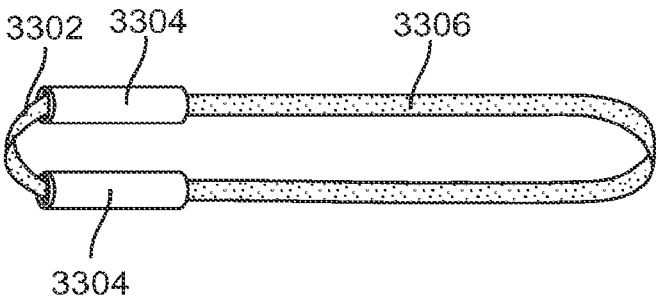
FIGS. 33A-33B illustrate several embodiments of con-
straint devices which may be attached to the coccyx.
Figure 33B:
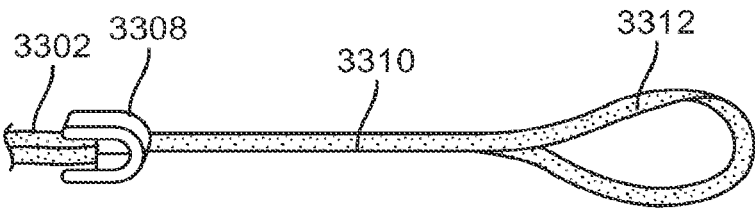

For example, the constraint device in FIG. 33A includes an extra long lower tether portion 3306 that can accommodate the additional distance required to be looped around the coccyx. The upper tether portion 3302 is shorter than the lower portion, but sized to be coupled with an upper spinous process. A pair of compliance members 3304 join the upper and lower tether portions. In FIG. 33B, the lower tether portion 3310 is a single tether having a looped end 3312 for looping around the coccyx. Additionally, a connector or shackle 3308 is attached to an upper part of the lower tether portion 3310 and allows the lower tether portion to be joined with a constraint device such as that illustrated in FIG. 2A.

Figure 34A:
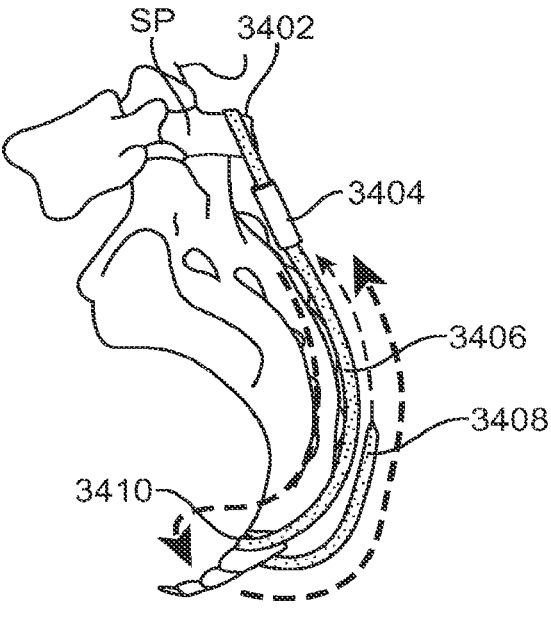
FIGS. 34A-34B illustrate surgical methods of coupling a
constraint device with the coccyx.
Figure 34B:
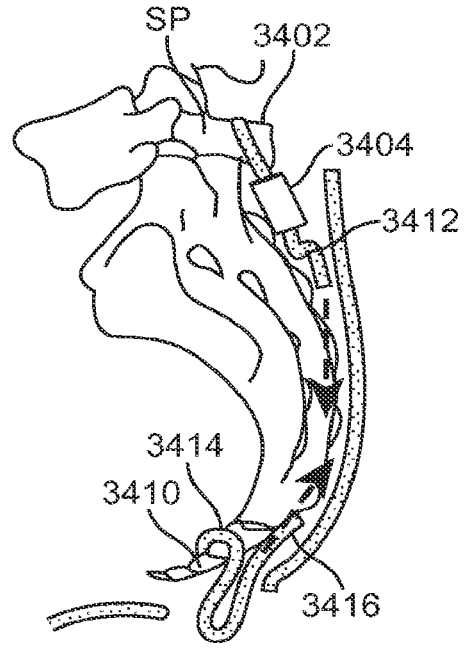

The constraint device may be coupled with the coccyx in several different surgical procedures such as those illustrated in FIGS. 34A-34B. For example, in FIG. 34A, an upper tether portion 3402 of the constraint device is coupled with a superior spinous process SP. An extra long lower tether portion 3406 is then advanced subcutaneously caudally toward the coccyx and then looped around the coccyx 3410. The free end 3408 of the lower tether portion is then advanced in the cranial direction and coupled with a compliance member 3404 which is also coupled with the upper tether portion 3402. In FIG. 34B, the upper tether portion 3402 is coupled with an upper spinous process SP. A second incision may be made and a lower tether portion 3414 is looped around the coccyx 3410 and the free end 3416 is advanced subcutaneously in the cranial direction wherein it will be connected to a tail 3412 on the compliance member 3404. Orthopedic cables, wires, sutures, band passing instruments are well known in the art and may be used to facilitate movement of the tethers While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for restricting flexion of a spinal segment of a patient, said method comprising:

providing a constraint device having a tether structure, the tether structure comprising an upper portion and a lower portion, the tether structure configured to restrict flexion of the spinal segment while allowing substantially unrestricted spinal extension;

coupling the upper portion of the tether structure to a spinous process of a superior vertebra in the spinal segment;

anchoring an anchor element to a sacrum of the patient inferior to the superior vertebra, wherein the anchor element comprises a plate having a plurality of protrusions, the plurality of protrusions configured to penetrate the sacrum, wherein anchoring the anchor element comprises anchoring the anchor element to the sacrum by the plurality of protrusions without using screws, and wherein anchoring the plurality of protrusions only penetrates cortical bone on a dorsal surface of the sacrum; and coupling the lower portion of the tether structure to an attachment feature on the anchor element.

* * * * *